United States Patent
Yen

(10) Patent No.: US 12,410,433 B2
(45) Date of Patent: *Sep. 9, 2025

(54) BUILDING DESIGNER RNA NANO-STRUCTURES FOR SYNTHETIC BIOLOGY APPLICATIONS

(71) Applicant: Baylor College of Medicine, Houston, TX (US)

(72) Inventor: Laising Yen, Pearland, TX (US)

(73) Assignee: Baylor College of Medicine, Houston, TX (US)

( * ) Notice: Subject to any disclaimer, the term of this patent is extended or adjusted under 35 U.S.C. 154(b) by 85 days.

This patent is subject to a terminal disclaimer.

(21) Appl. No.: 18/176,868

(22) Filed: Mar. 1, 2023

(65) Prior Publication Data

US 2023/0332161 A1    Oct. 19, 2023

Related U.S. Application Data

(63) Continuation of application No. 16/348,445, filed as application No. PCT/US2017/061186 on Nov. 10, 2017, now Pat. No. 11,597,935.

(60) Provisional application No. 62/420,085, filed on Nov. 10, 2016.

(51) Int. Cl.
| | |
|---|---|
| *C12N 15/115* | (2010.01) |
| *C07H 21/02* | (2006.01) |
| *C12N 15/10* | (2006.01) |
| *C40B 40/06* | (2006.01) |
| *B82Y 5/00* | (2011.01) |
| *B82Y 40/00* | (2011.01) |

(52) U.S. Cl.
CPC ........... *C12N 15/115* (2013.01); *C07H 21/02* (2013.01); *C12N 15/1093* (2013.01); *C40B 40/06* (2013.01); *B82Y 5/00* (2013.01); *B82Y 40/00* (2013.01); *C12N 2310/51* (2013.01); *C12N 2310/531* (2013.01)

(58) Field of Classification Search
None
See application file for complete search history.

(56) References Cited

U.S. PATENT DOCUMENTS 11,597,935 B2 * 3/2023 Yen ............ C12N 15/115
2012/0263648 A1  10/2012 Shapiro et al.

OTHER PUBLICATIONS

Shu et al. Nat Nanotechnol 6:658-667 (Year: 2011).*
Parlea et ak. Methods 103 128-137, Jul. 2016 (Year: 2016).*
Grabow et al. Nano Lett. 2011 11:878-887, pp. 1-22 (Year: 2011).*
Addgene: CRISPR guide, https://www.addgene.org/guides/crispr/, retrieved on-line Oct. 2, 2024, pp. 1-19 (Year: 2019).*
Durbin et al. Molecules 24, 37 40, pp. 1-13 (Year: 2019).
Hao et al. RNA Biology 13, 635-645 (Year: 2016).
Haque et al. WIREs RNA e1452, pp. 1-17 (Year: 2017).
Liu et al. chemrxiv.org, retrieved on-line on Apr. 19, 2022 from https://chemrxiv.org/engage/api-gateway/chemrxiv/assets/orp/resource/ item/60c 7 40cbbdbb89b4efa38203/original/ branched-kissing-loops-for-the-construction-of-diverse-rna-homooligomeric-nanostructures.pdf pp. 1-22 (Year: 2019).
Shu et al. Nano Letters vol. 4, 1717-1723 (Year: 2004).

* cited by examiner

*Primary Examiner* — Brian Whiteman
(74) *Attorney, Agent, or Firm* — Norton Rose Fulbright US LLP

(57) ABSTRACT

Embodiments of the disclosure include compositions and methods for generating RNA nanostructures, particularly in a cell. In particular embodiments, RNA subunits comprising at least one three-way junction and at least one kissing loop are configured such that multiple RNA subunits can polymerize into a specific structure. In particular embodiments, the RNA subunits are configured such that sequence of at least one kissing loop is complementary to sequence of another kissing loop, such as on another RNA subunit, and the summation of multiple RNA subunits having specific individual structures results in a combined polymerized structure of a defined shape. In specific embodiments, an RNA nanostructure generated from methods herein is utilized for an application, such as manufacturing or genetic modifications in a cell.

7 Claims, 49 Drawing Sheets

Specification includes a Sequence Listing.

An example of kissing-loop employed in our study derived from HIV kissing loops
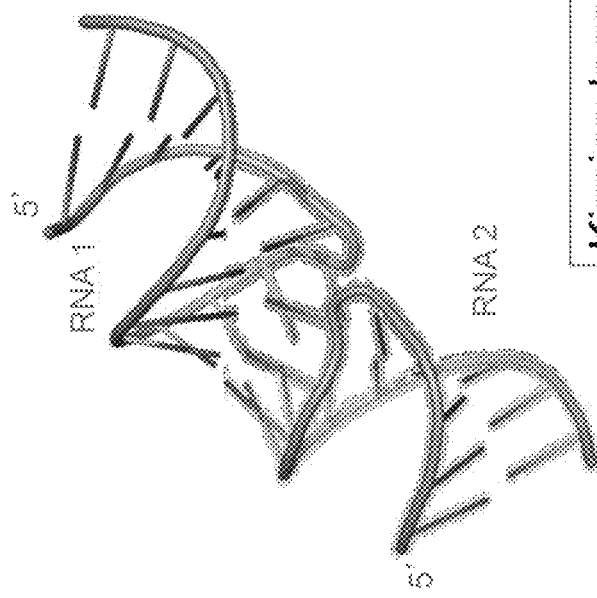
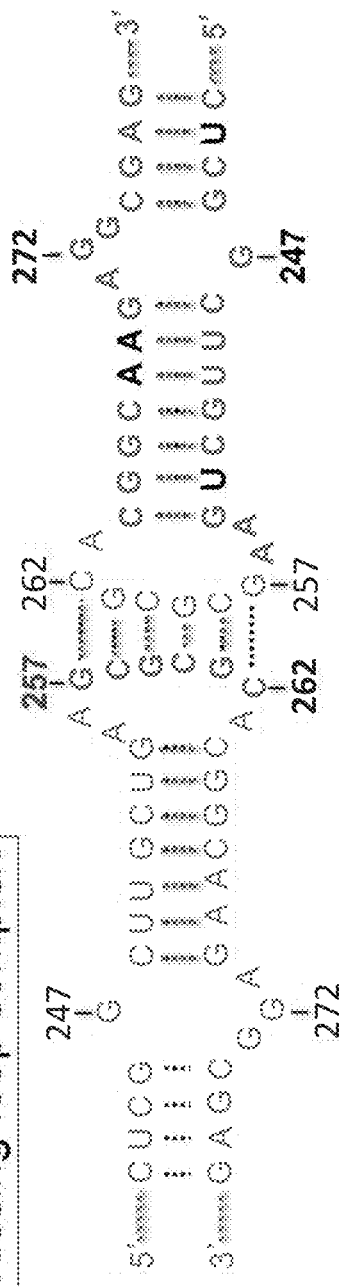
FI

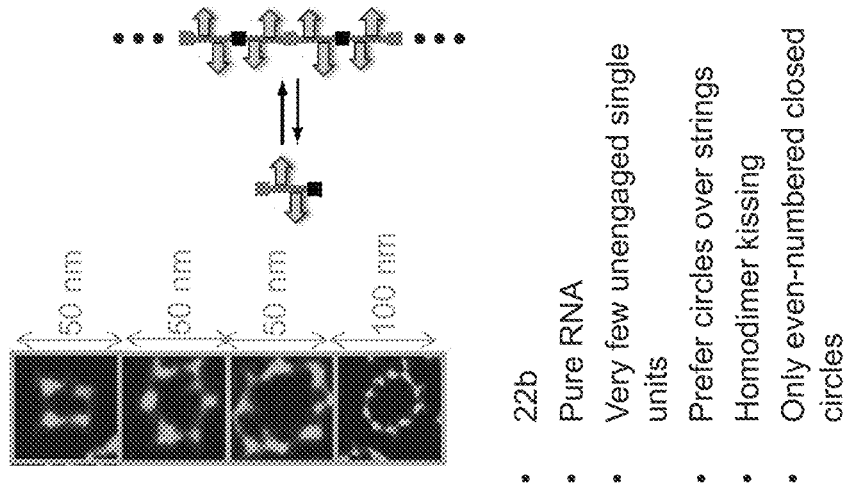
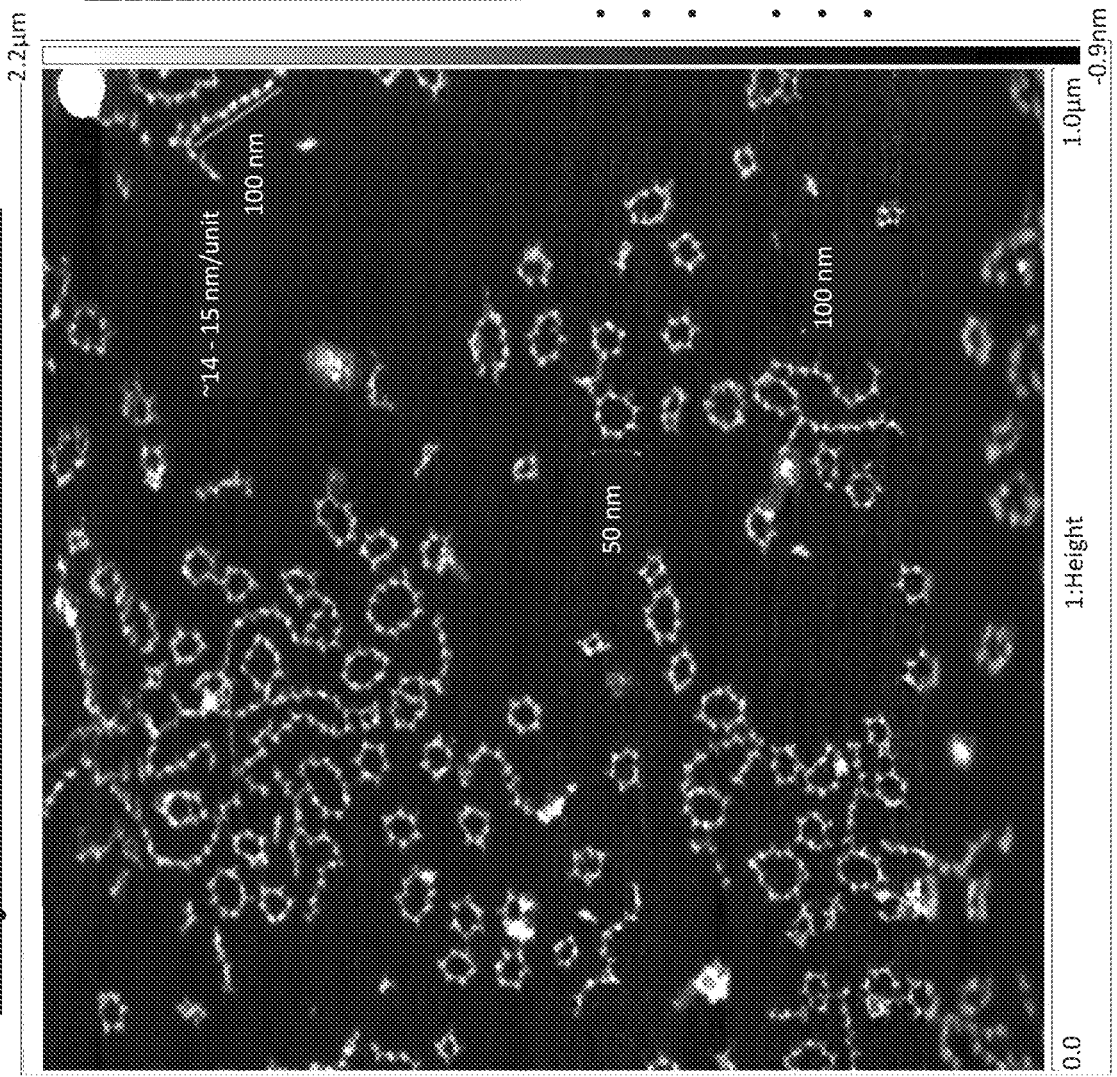
FIG. 3

Single unit with disabled kissing loops
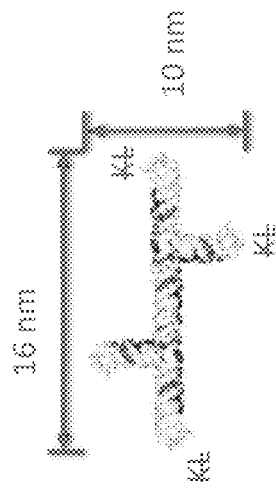
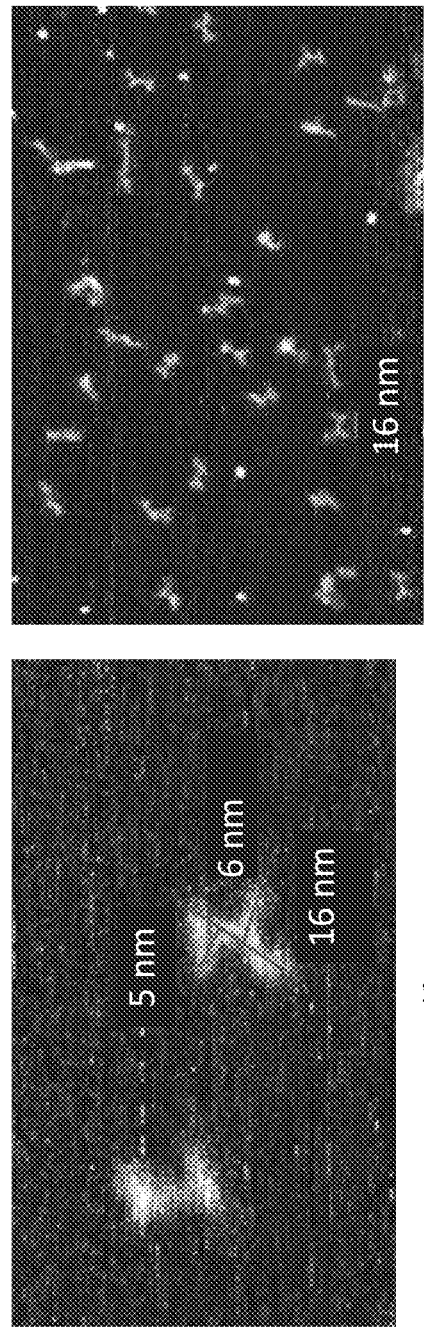
FIG. 4

Polymerization with three kissing-loops
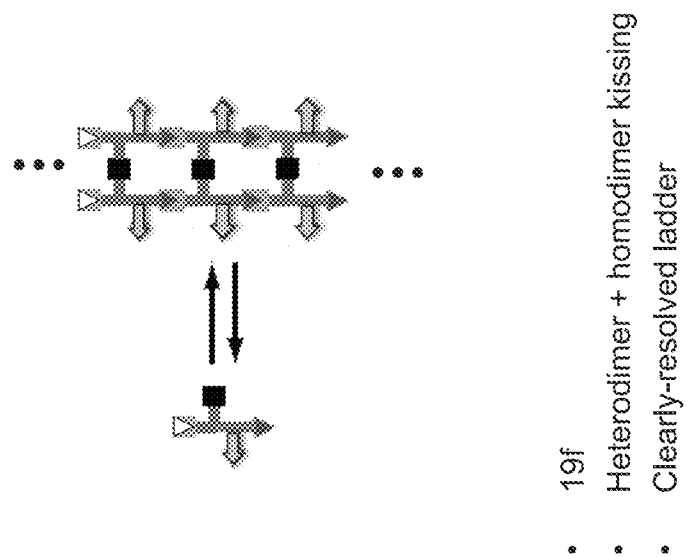
- 19f
- Heterodimer + homodimer kissing
- Clearly-resolved ladder
59 nm = 15 nm per unit
FIG. 7A

Single unit with 4 kissing loops

Bone-shape, in-plane geometry, with Z arm 3 three-way junctions, 4 kissing loops Allows polymerization in X and partially Y direction

1.5D Ladder formation with four kissing loops
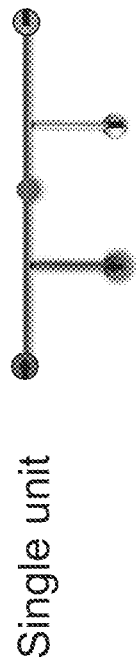
Single unit
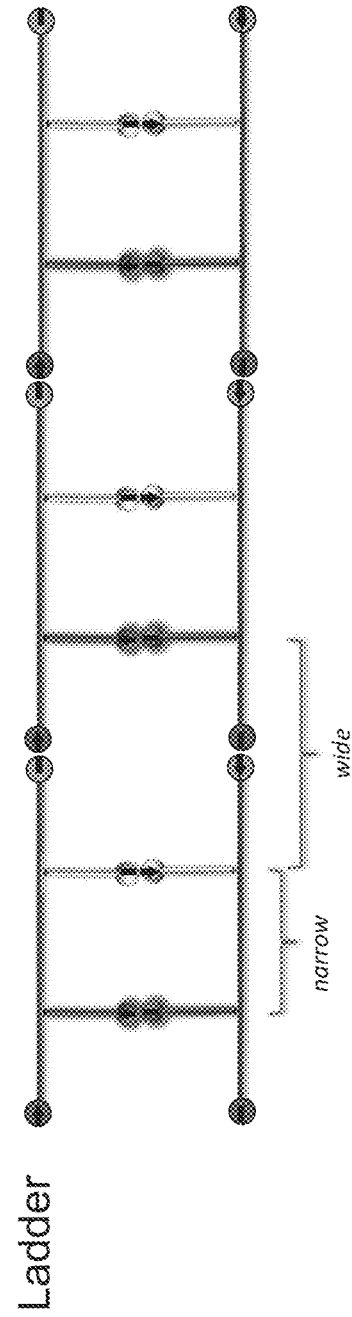
Ladder
FIG. 8B

1.5D Ladder formation with four kissing loops
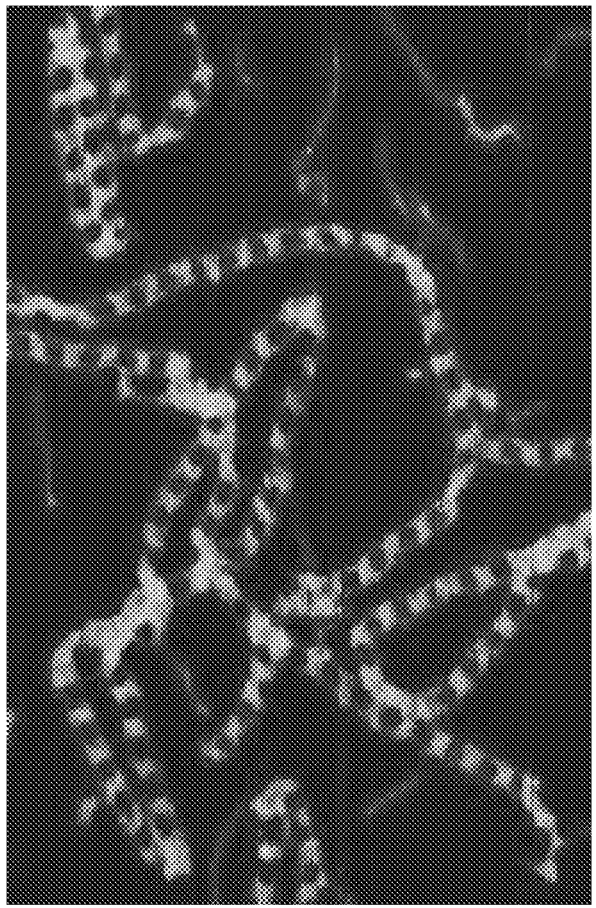
- 24a
- Heterodimer + homodimer kissing
- Clearly-resolved ladder
- Stable in both wet and dry condition
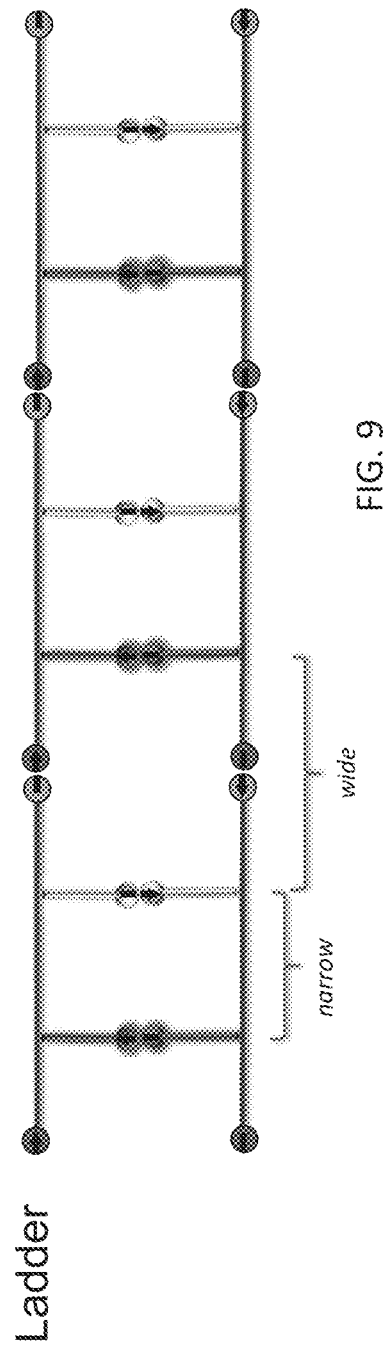
Ladder
FIG. 9

Single unit with 4 kissing loops

- Bone-shape, in-plane geometry, with Z arm
- 3 three-way junctions, 4 kissing loops
- Allows polymerization in X and Y directions Effect of kissing loop twist

Expressing single RNA unit in human cells

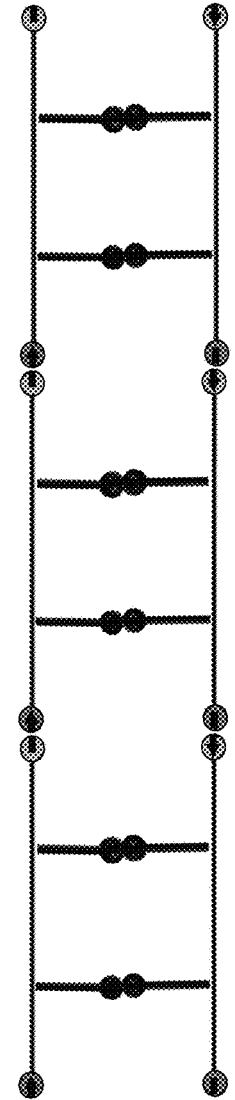

24a (no tail) Active KL

24e (no tail) Inactive KL

Expressed single RNA units with inactive kissing loops are unstable in cells (lane 2). In contrast, single RNA units with active kissing are highly stable (lane 1). This suggests that the formation of higher order nanostructures protect the engaged single RNA units in cells.

Northern RNA gel

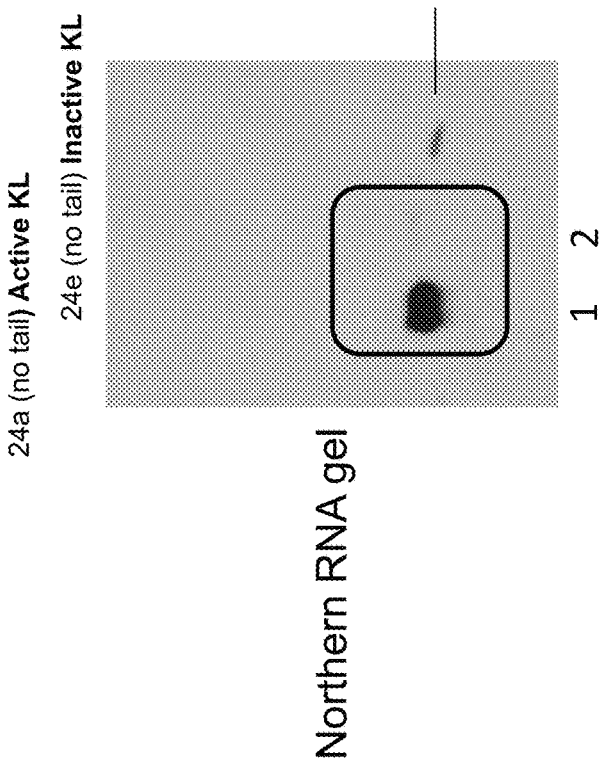

Single unit

FIG. 16

One application: maximize oil droplet production in green microalga Chlamydomonas
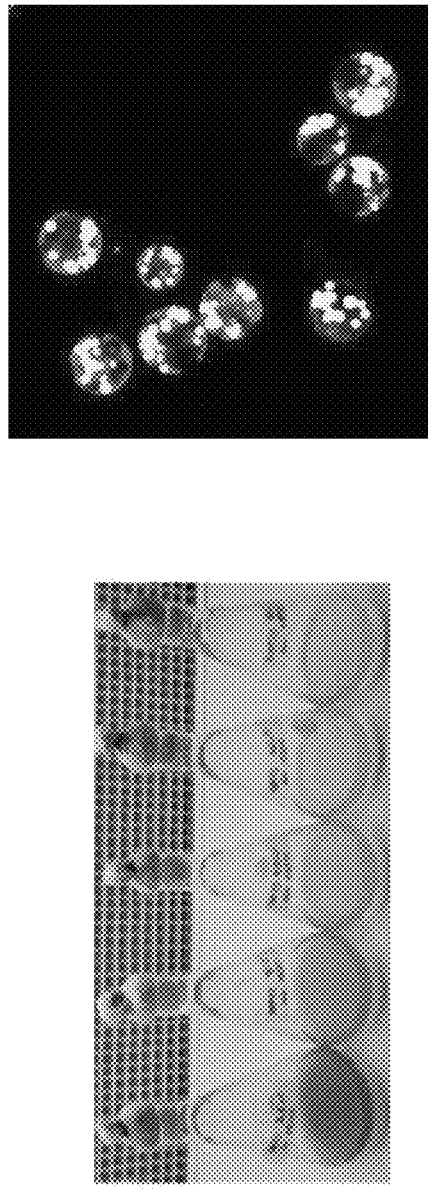
Highly structured RNA scaffolds could be used to anchor specific set of enzymes at fixed proximity to maximize the efficiency of biosynthesis in algal biofuel production
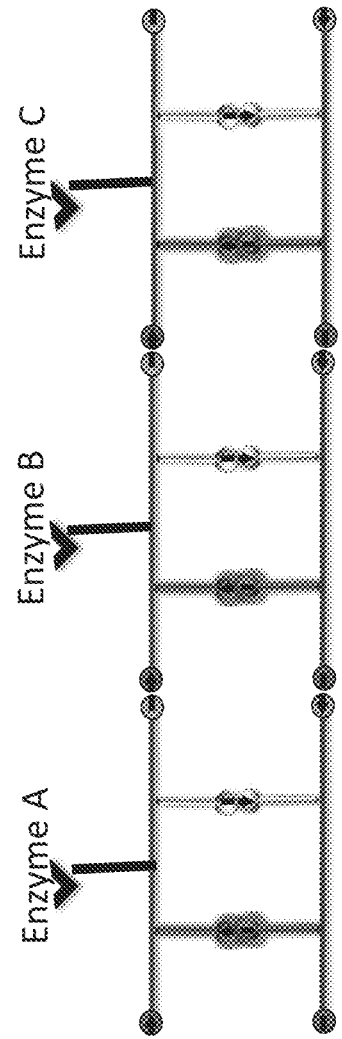
FIG. 19 inactive KL

FIG. 21
CONTINUED

BUILDING DESIGNER RNA NANO-STRUCTURES FOR SYNTHETIC BIOLOGY APPLICATIONS

CROSS-REFERENCE TO RELATED APPLICATIONS

This application is a continuation of U.S. Non-Provisional application Ser. No. 16/348,445 filed May 8, 2019, which is a national phase application under 35 U.S.C. § 371 that claims priority to International Application No. PCT/US2017/061186 filed Nov. 10, 2017, which claims priority to U.S. Provisional Patent Application Ser. No. 62/420,085, filed Nov. 10, 2016, which is incorporated by reference herein in its entirety.

INCORPORATION OF SEQUENCE LISTING

The instant application contains a Sequence Listing, named "SL_BAYMP0213USC1" (20,019 bytes; created Mar. 1, 2023) which has been submitted electronically in XML format and is hereby incorporated by reference in its entirety.

TECHNICAL FIELD

Embodiments of fields of the subject matter of the disclosure include at least cell biology, molecular biology, biochemistry, and medicine.

BACKGROUND

RNAs are highly programmable polymers due to their ability to form specific Watson-Crick base pairing, a property that can be exploited to create well-defined 2D and 3D structures. These structures are thermodynamically stable, and formed via spontaneous self-assembly, a process that requires no catalytic co-factors. In contrast to DNA, single-stranded RNA can be efficiently expressed at high levels in live cells, thus offers the opportunity to program cells to assemble designer nanostructures.

The present disclosure satisfies a long-felt need in the art for utilizing nanostructures at least for biological engineering purposes.

BRIEF SUMMARY

The present invention is directed to systems, methods, and compositions to produce structures from RNA molecules. In particular embodiments, structures of an ordered shape are produced from RNA molecules, and in specific embodiments the structures are generated in the absence of one or more agents, such as in the absence of one or more catalysts and/or co-factors of any kind and/or in the absence of one or more conditions. In specific aspects the structures are formed via spontaneous self-assembly. In specific embodiments, the structures and/or their RNA subunits have a designed shape that is not produced randomly. The structures may be designed to have a particular shape based on the sequence of the RNA from which they are generated, and this designed structure is produced only because particular selected RNA sequences were utilized. In particular embodiments, DNA molecules are not employed. However, DNA/RNA hybrid structures can be designed using similar engineering principles for specific applications.

Methods of the disclosure may include the step of designing the primary sequence of the RNA molecule(s) such that one or more particular structures are produced. The RNA molecules and/or any structure(s) produced therefrom are not found in nature. The RNA molecules and/or any structure(s) produced therefrom are synthetic.

In particular embodiments, the structures are nanostructures, although their assembled size may be on the order of micrometers. The structures may be one-dimensional (1D), one and a half-dimensional (1.5D), two-dimensional (2D), or three-dimensional (3D).

In specific embodiments, one or more structures are produced from RNA molecules in any suitable environment, including a cell. Any type of cell may be utilized for production of the structures, including eukaryotic or prokaryotic, and including mammalian, bacterial, or algal, for example.

In one embodiment, there is a synthetic RNA molecule, comprising at least one three-way junction and at least one kissing loop. In specific cases, the molecule is double stranded (ds) except for one or more of the following: the kissing loop; base of the three-way junction; a single stranded tail; and/or a single stranded tail with 5' and 3' end closed by ligation such that the subunit is a circular RNA. The three-way junction is derived from ribosomal L1 RNA three-way junction, riboswitches, ribozymes, virus, or pRNA, in at least some cases. In specific embodiments, the kissing loop is derived from HIV or another virus kissing loop or a kissing loop developed by in vitro evolution. The molecule comprises an in-plane geometry, in certain embodiments and it may lack a cellular signal, such as lack a splice site, polyA signal, and/or a known protein-binding domain (such as a CUG repeat).

In particular embodiments, the RNA molecule comprises 2, 3, 4, 5, or more three-way junctions. The RNA molecule may comprise 2, 3, 4, 5, or more kissing loops, and the kissing loop may be 6 or more nucleotides in length. In specific cases, 6 nucleotides of the kissing loop are capable of intermolecular interaction. The molecule may be at least 20, 25, 30, 35, 40, 45, 50, 55, 60, 65, 70, 75, or more nucleotides in length. In specific embodiments, the molecule is at least 7 nanometers in length and may be 16 nanometers in length, as an example. In specific cases, the molecule is at least 7 nanometers in width, for example 10 nanometers in width. The molecule may be polymerizable from an end, for example the molecule may be polymerizable from a kissing loop. In some cases an RNA subunit has its 5' and 3' ends ligated to one another.

In particular embodiments of the RNA molecule, nucleotides in a kissing loop on a first end of the molecule are complementary in sequence to a kissing loop in a second end of the molecule. The length of complementary sequence may be flexible as long as they provide sufficient stability for interaction. In certain cases, the molecule has one or more arms of a three-way junction that lacks a kissing loop sequence that is capable of specific kissing interaction with another RNA molecule that has a kissing loop on its arm. The molecule may be a single unit comprising a generally bone shape or any derivative of a bone shape with branching geometry. In specific embodiments, one or more kissing loops of the molecule lack the ability to complement a kissing loop on another RNA molecule. In some cases, two or more three-way junctions in the molecule are configured to position two or more kissing loops on the same side of the molecule in a plane.

In one embodiment there is a plurality of RNA molecules, wherein at least two RNA molecules are bound to each other through complementary binding of a kissing loop on each RNA molecule. The plurality may be configured in a linear string of molecules or configured in the shape of a circle, as examples. In specific embodiments, in the plurality of RNA molecules a first arm of a first three-way junction lacks the ability to complement a kissing loop on another RNA molecule and a first arm on a second three-way junction lacks the ability to complement a kissing loop on another RNA molecule. In specific embodiments, the circle comprises an even number of RNA molecules or it can comprise an odd number of RNA molecules. In regards to some pluralities of RNA molecules, whether or not the circle has even or add number of RNA molecules is determined by whether the kissing loops are designed to engage in homodimer or heterodimer kissing loop interaction. In a specific embodiment, each of the RNA molecules in a plurality comprises two three-way junctions and two kissing loops and the plurality is configured in the shape of a square. Each of the RNA molecules in the plurality may comprise three three-way junctions and four kissing loops, wherein two or more of the three-way junctions in the molecule are configured to position two or more kissing loops on the same side of the molecule in a plane, and wherein the plurality is configured in the shape of a ladder. In certain embodiments, at least one arm of a three-way junction projects perpendicularly to the plane and the arm that projects perpendicularly to the plane may be polymerizable with additional RNA molecules. In particular embodiments, the length of the molecule between two of the junctions in the molecule is not the same length of an arm of the molecule between one end of the molecule and a three way junction closest to that end. Each of the RNA molecules in a plurality may comprise three three-way junctions and four kissing loops, wherein two or more of the three-way junctions in the molecule are configured to position two or more kissing loops on different sides of the molecule in a plane, and wherein the plurality is configured in the shape of a two-dimensional grid. The plurality may have the ability to self-assemble in non-linear and/or non-perpendicular direction based on a specific design requirement.

In one embodiment, there is method of producing a structure of a plurality of RNA molecules encompassed by the disclosure, comprising the step of designing RNA molecules to complementarily bind to another RNA molecule in at least one kissing loop region under suitable conditions. In at least some cases, the conditions are suitable for self-assembly of the RNA molecules into the plurality. The conditions may be isothermal conditions. The conditions may comprise a temperature greater than freezing, such as being room temperature or 37° C., for example.

In specific embodiments, the RNA molecules self-assemble into the structure by binding only in a linear direction. The RNA molecules may self-assemble into the structure by binding in a linear direction and in a direction perpendicular to the linear direction or at an angle from the linear direction. The RNA molecules may self-assemble into the structure by binding in a linear direction and/or in a non-linear direction. In some cases, the linear direction and the direction perpendicular to the linear direction may be within a plane.

Embodiments of the disclosure include methods wherein the RNA molecules self-assemble into the structure by binding in a linear direction and in a direction perpendicular to the linear direction, wherein the linear direction and the direction perpendicular to the linear direction are within a plane, and also RNA molecules bind in a direction that is perpendicular to the plane and in a 90 angle from the plane. In at least some cases the method lacks a denature-renature cycle, an enzyme, a co-factor, or a combination thereof. Any method can occur in a cell, including a eukaryotic or prokaryotic cell. The cell may be a mammalian cell, bacterial, yeast, an algal cell, or an artificial cell with minimum organelles enclosed by a membrane, for example.

Embodiments of the disclosure include any structure produced by any one of the methods encompassed by the disclosure. In particular embodiments there is a structure comprising a plurality of RNA units configured in a pattern of one, two, or three dimensions, wherein the RNA units comprise one or more RNA molecules, wherein the one or more RNA molecules comprise at least one three-way junction and at least one kissing loop. The molecule may be double stranded except for the kissing loop.

In particular embodiments, there is a cell comprising any RNA molecules encompassed by the disclosure, any plurality of RNA molecules encompassed by the disclosure, or any structure encompassed by the disclosure.

In one embodiment, there is a method of producing a structure encompassed by the disclosure, comprising the steps of providing RNA molecules encompassed by the disclosure or a plurality of RNA molecules encompassed by the disclosure; and subjecting the RNA molecules to suitable conditions to allow them to self-assemble to the structure. The method may occur in vitro or in vivo. The method may occur in a cell. In specific embodiments, the method comprises the step of expressing the RNA molecules in the cell. In specific cases, at least one RNA molecule is expressible from an expression vector. The cell may be prokaryotic or eukaryotic. In specific embodiments, the structure binds to a region of a chromosome or organelle in the cell, such as nucleic acid in an organelle in the cell. In certain embodiments, the structure binds to the chromosome through a single stranded region of the RNA molecule. The method may comprise targeting of the structure to the chromosome using the CRISPR-Cas9 system, such as the chromosome being a somatic chromosome or a sex chromosome. Some methods include the step of affixing at least one agent to the structure, such as via an aptamer or a set of aptamers that replaces a kissing loop at the end of an arm in a X, Y, or Z direction. The aptamer may bind one or more specific molecules, such as a protein, for example an enzyme. The structure may bind at least one telomere of the chromosome and at least in some cases the binding of the structure to the telomere results in control of the telomere function. An agent may be a protein, peptide, nucleic acid, small molecule, or combination thereof. Cells used in the method may be an algal cell and the agent may be a protein, such as one or more enzymes for biofuel production.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIG. 1A provides an example of an RNA subunit, such as having two three-way junctions and three kissing loops. FIG. 1B shows an example of a three-way junction, here derived from ribosomal L1 RNA. FIG. 1C provides an example of a kissing loop, such as one derived from HIV kissing loops (illustrated with SEQ ID NO:9 and SEQ ID NO: 10).

FIG. 3 demonstrates imagery of polymerization in a X-direction.

FIG. 4 shows a single RNA subunit having disabled kissing loops and imagery of same.

FIGS. 7A and 7B. FIG. 7A demonstrates visualization of polymerization with subunits having three kissing loops. FIG. 7B provides an example of a non-denaturing RNA gel with different structures including a control with a subunit having inactive kissing loops.

FIGS. 8A and 8B. FIG. 8A is an illustration of a single unit with 4 kissing loops.

FIG. 8B illustrates a 1.5D ladder formation with RNA subunits having four kissing loops.

FIG. 9 shows visualization of a 1.5D ladder formation with RNA subunits having four kissing loops.

FIG. 16 demonstrates expression of single RNA subunits in human cells.

FIG. 18A provides visualization of the stable expression of structures wherein the RNA subunits have active kissing loops, whereas in FIG. 18B the subunits had inactive kissing loops.

FIG. 19 illustrates an example wherein oil droplet production in green microalga *Chlamydomonas* is maximized using RNA structures having enzyme(s) for the production linked thereto.

DETAILED DESCRIPTION

Figure 1A:
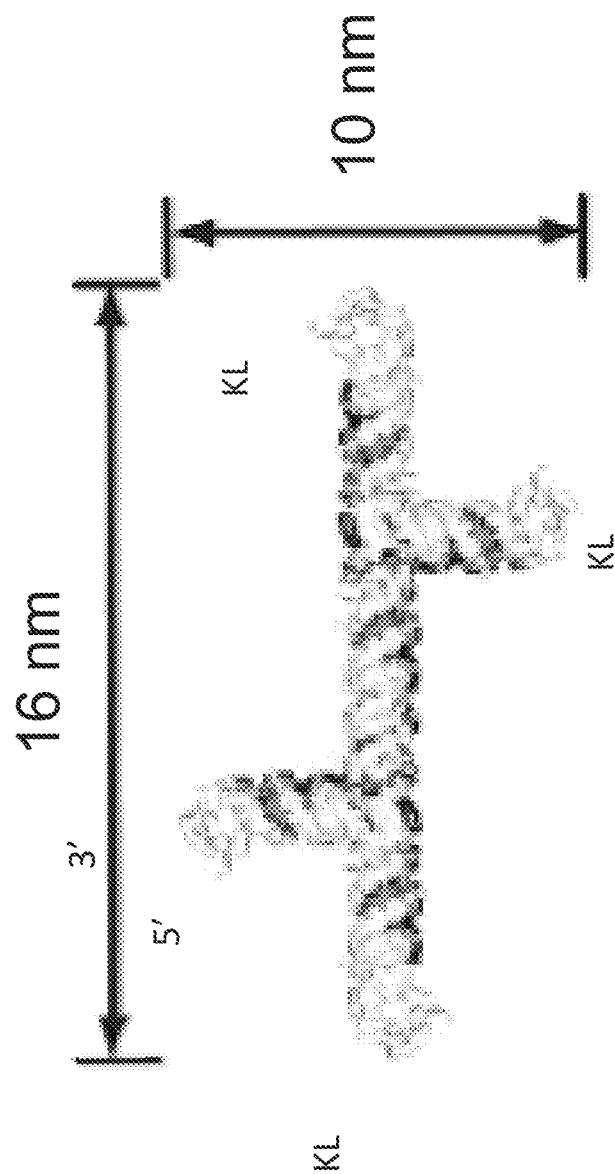
FIGS. 1A and 1B.

As used herein the specification, "a" or "an" may mean one or more. As used herein in the claim(s), when used in conjunction with the word "comprising", the words "a" or "an" may mean one or more than one. As used herein "another" may mean at least a second or more. Still further, the terms "having", "including", "containing" and "comprising" are interchangeable and one of skill in the art is cognizant that these terms are open ended terms. Some embodiments of the disclosure may consist of or consist essentially of one or more elements, method steps, and/or methods of the disclosure. It is contemplated that any method or composition described herein can be implemented with respect to any other method or composition described herein.

As used herein, the term "kissing loop" (which may also be referred to in the art as a kissing stem-loop) refers to when unpaired nucleotides in one hairpin loop base pair with unpaired nucleotides in another hairpin loop.

Embodiments of the disclosure encompass building of designer RNA structures, including nanostructures, and in specific embodiments the structures are utilized for an application, such as a biological application. Unlike proteins, RNAs are highly programmable polymers because of their ability to form specific Watson-Crick base pairing, a property that can be exploited to generate well-defined 1D, 2D, and 3D structures, for example. These structures are thermodynamically stable and form via spontaneous self-assembly, a process that requires no catalytic co-factors, in certain embodiments. In contrast to DNA, single-stranded RNA can be efficiently expressed at high levels in live cells, thus offering the opportunity to program cells to assemble designer nanostructures.

By considering the RNA sequences and RNA domains to be used, one can develop a useful RNA single unit design that can self-assemble into higher order architectures, reaching a size of micrometers, in some embodiments. Depending on specific configuration(s) used, these repeating RNA units assemble spontaneously into precisely organized structures including, for example, 1D strings and circles, 1.5D ladders, and 2D grids in isothermal condition without the denature-renature cycles. They are very stable, as they maintain their structural integrity in wet and dry condition.

The results demonstrated herein indicate that RNA can be used to program mammalian cells to assemble designer nanostructures for specific cellular functions useful for any one of synthetic biology applications. The disclosure encompasses genetically encodable higher order RNA nanostructures useful for programming cells to assemble designer nanostructures for specific cellular functions or for synthetic biology applications. In particular, depending on specific configurations used, these repeating RNA single units assembled spontaneously into precisely organized 1D strings and circles, 1.5D ladders, and 2D grids in isothermal condition without the denature-renature cycles. When these RNA single units were expressed in cells, they appeared to form stable higher order structures. Furthermore, RNA single units are genetically encodable and can be expressed by plasmids, viral vectors, or directly from engineered genome.

This lays the technological foundation for higher order RNA nanostructures useful for programming cells to assemble designer nanostructures for specific cellular functions or for synthetic biology applications.

I. RNA Structured Compositions and Methods of Producing Same

Embodiments of the disclosure include at least RNA subunits, polymers comprising 2 or more RNA subunits, structures generated therefrom, and methods of making and/or using them. The RNA subunits each at least have one three-way junction and one kissing loop that is not inactivated, in specific embodiments. In at least some cases, the three-way junction(s) of a particular RNA subunit provides the geometry of the subunit, and the kissing loop (KL) is an active site that is used for the interaction between two (or more) units.

In particular embodiments, RNA that is expressed in cells generates a dsRNA scaffold to minimize mis-foldings and mis-interactions. In certain embodiments, ssRNA is not utilized to avoid interference with other molecules. Thus, in particular embodiments the RNA molecules lack ssRNA sequences, although in certain embodiments the RNA molecules comprise ssRNA sequences. The RNA molecules are capable of undergoing spontaneous self-assembly, including in isothermal conditions at 37° C. In specific aspects the RNA molecules are not subject to a denature-renature cycle. In specific embodiments, the RNA is devoid of one or more cellular signals, such as devoid of a splice site, a polyA signal, and/or devoid of a protein domain. In alternative embodiments, the RNA may comprise one or more cellular signals and in such cases, the cellular signal(s) may be present in the RNA but not by design.

In particular embodiments, an RNA molecule utilized in compositions and methods of the disclosure comprise, consist of, or consist essentially of one or more three-way junctions (for example from rRNA, riboswitches, ribozymes, viruses, and/or pRNA) and one or more kissing loops (for example from HIV virus and other viruses, and kissing developed by in vitro evolution. In fact, any two loops with complimentary in sequence that allow stable interactions can be used. In a plurality of RNA subunits of the disclosure (for example, in a single structure), all (or in some cases less than all) of the RNA subunits comprise, consist of, or consist essentially of one or more three-way junctions and one or more kissing loops. In specific embodiments, in a plurality of RNA subunits, the majority of RNA subunits comprise, consist of, or consist essentially of one or more three-way junctions and one or more kissing loops. In a plurality of RNA subunits, at least 70, 75, 80, 85, 90, 91, 92, 93, 94, 95, 96, 97, 98, or 99% of RNA molecules comprise, consist of, or consist essentially of one or more three-way junctions and one or more kissing loops. In specific cases, the RNA molecules lack ssRNA sequences except in the kissing loop(s).

An RNA molecule may comprise, consist of, or consist essentially of at least two RNA subunits. An RNA molecule may comprise, consist of, or consist essentially of multiple RNA subunits, such as at least 2, 3, 4, 5, 6, 7, 8, 9, 10, 25, 30, 35, 40, 45, 50, 75, 100, 250, 500, 750, 1000, or more subunits. The number of RNA subunits in a higher order structure is limited only by the cellular compartments where they are expressed. In specific cases, an RNA molecule comprises, consists of, or consists essentially of at least or no more than between 2 and 1000, 2 and 750, 2 and 500, 2 and 250, 2 and 100, 2 and 75, 2 and 50, 2 and 25, 2 and 10, 2 and 5, 5 and 1000, 5 and 750, 5 and 500, 5 and 250, 5 and 100, 5 and 75, 5 and 50, 5 and 25, 5 and 10, 10 and 1000, 10 and 750, 10 and 500, 10 and 250, 10 and 100, 10 and 75, 10 and 50, 10 and 25, 25 and 1000, 25 and 750, 25 and 500, 25 and 250, 25 and 100, 25 and 75, 25 and 50, 50 and 1000, 50 and 750, 50 and 500, 50 and 250, 50 and 100, 50 and 75, 75 and 1000, 75 and 500, 75 and 250, 75 and 100, 100 and 1000, 100 and 750, 100 and 500, 100 and 250, 250 and 1000, 250 and 750, 250 and 500, 500 and 1000, 500 and 750, or 750 and 1000 RNA subunits.

In particular embodiments, an RNA subunit is of a particular size including particular dimensions. In some cases the RNA subunit is at least 7, 8, 9, 10, 11, 12, 13, 14, 15, 16, 17, 18, 19, 20, or more nanometers in length and/or in some cases the RNA subunit is at least 7, 8, 9, 10, 11, 12, 13, 14, 15, 16, 17, 18, 19, 20, or more nanometers in width.

In specific embodiments, the RNA subunit is at least 20, 25, 30, 35, 40, 45, 50, 55, 60, 65, 70, 75, 100, 125, 150, 175, 200, 225, 250, 300, or more nucleotides in length.

Figure 1B:
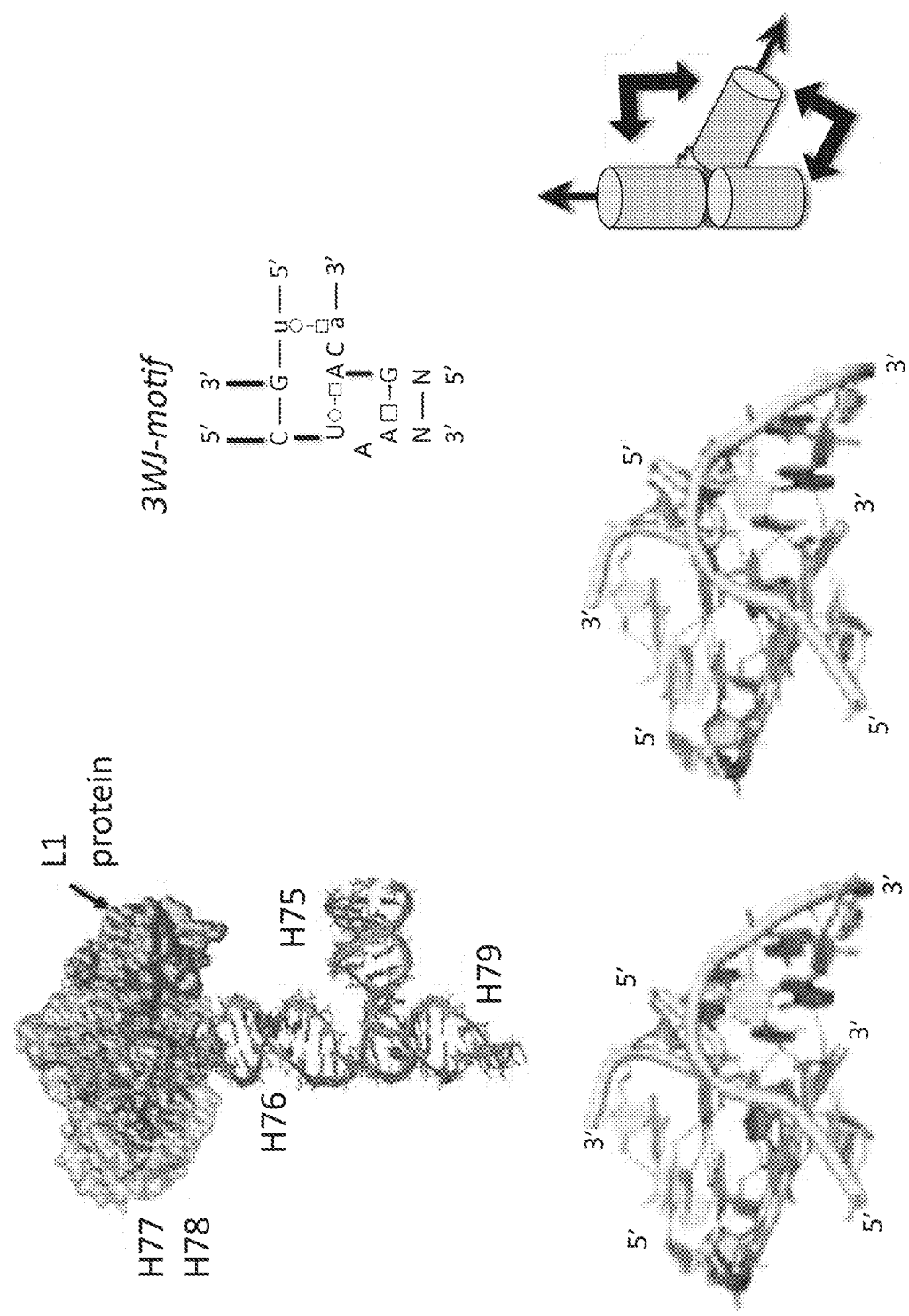

In an RNA subunit, there may be a certain number of three-way junctions and a certain number of kissing loops. The RNA subunit itself may or may not comprise in-plane geometry The RNA may or may not comprise a generally bone shape. The RNA subunit (and therefore the RNA molecule that comprises it) may lack alternative folding or have minimized alternative folding because of its sequence design. In specific embodiments, an RNA subunit may comprise, consist of, or consist essentially of two three-way junctions and three kissing loops (see FIG. 1A). Referring to FIG. 1A, an RNA subunit may have a length greater than its width (or vice versa in other cases). An RNA subunit may comprise of at least one three-way junction (FIG. 1B) and one kissing loop (FIG. 1C). The RNA subunit in FIG. 1 may comprise two three-way junctions and three kissing loops (KL). In one subunit, the 5' end and the 3' end of the single RNA molecule of the subunit may be adjacent to one another in relation to the entire subunit geometry, or the 5' end and the 3' end are closed by ligation forming a circular RNA subunit. One can routinely visualize individual RNA subunits or assembled higher order RNA molecules comprising multiple RNA subunits using atomic force microscopy (AFM). In addition, they can be visualized by high-resolution electron microscope, or analyzed by gel shifting assay, for example.

Figure 2:
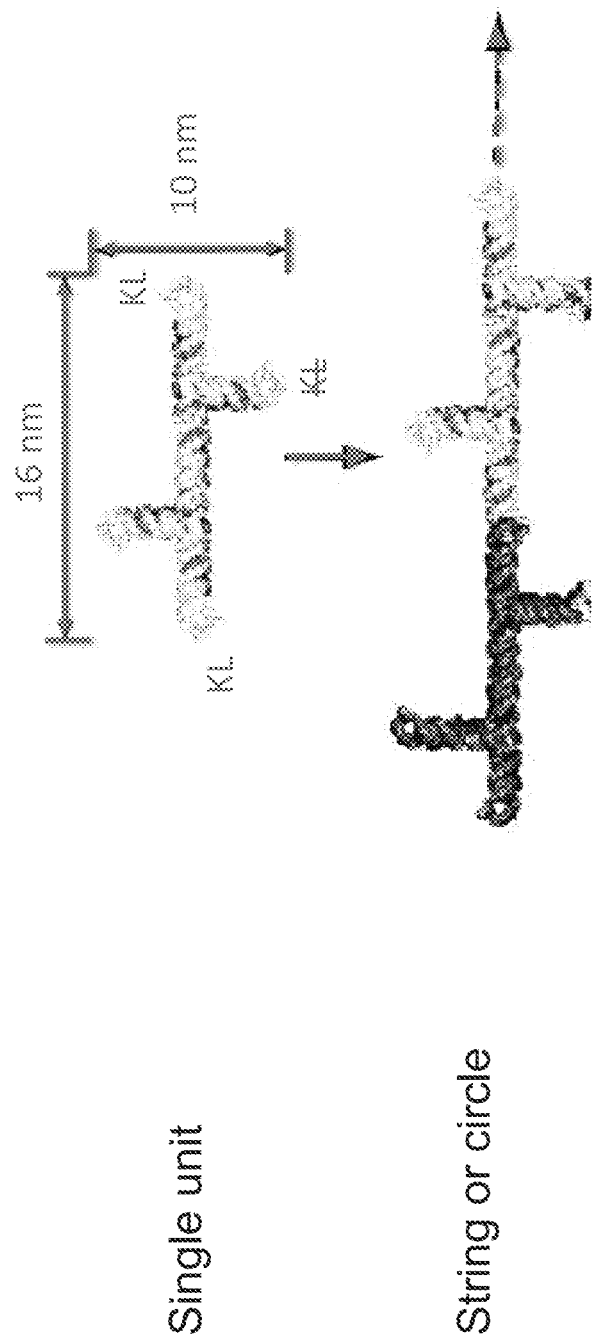
FIG. 2 shows an example of polymerization in an X-direction.

FIG. 2 illustrates polymerization of an example of a single RNA subunit. In specific embodiments, RNA subunits are designed such that they become polymerized at their ends with other RNA subunits through design of the sequence of their respective kissing loops. For example, as in FIG. 2, one end of one RNA subunit is able to bind another end of another RNA subunit, and this polymerization along an x-axis generates an RNA molecule that manifests a particular structure, such as a string or circle. FIG. 3 demonstrates specific examples of circles generated upon polymerization of specifically designed RNA subunits. FIG. 3 also demonstrates cases wherein circles of different sizes are generated dependent upon the number of RNA subunits.

In specific cases, an RNA molecule that is a polymer of RNA subunits comprises multiple units of the same RNA subunit having the same sequence and structure. In other cases, an RNA molecule that is a polymer of RNA subunits comprises multiple units of different RNA subunits having different sequence (that may or may not have the same general structure, such as generally bone shaped, for example). In cases in which closed circles are generated, there may be an even number of RNA subunits therein, or odd number depending on the kissing loops employed.

FIG. 4 illustrates an RNA subunit comprising disabled kissing loops. In such cases, ordered structures may be unable to be formed. In other cases, a particular structure is produced at least in part because of one or more disabled kissing loops in an RNA subunit when at least one other kissing loop in the RNA subunit is functional.

Figure 5:
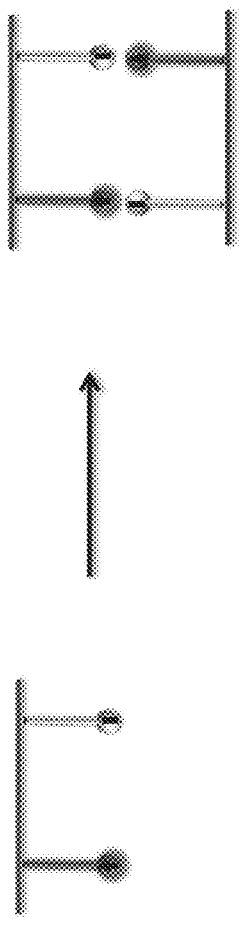
FIG. 5 illustrates a single RNA subunit having two kissing loops and 2 three-way junctions to produce a square structure.
Figure 6:
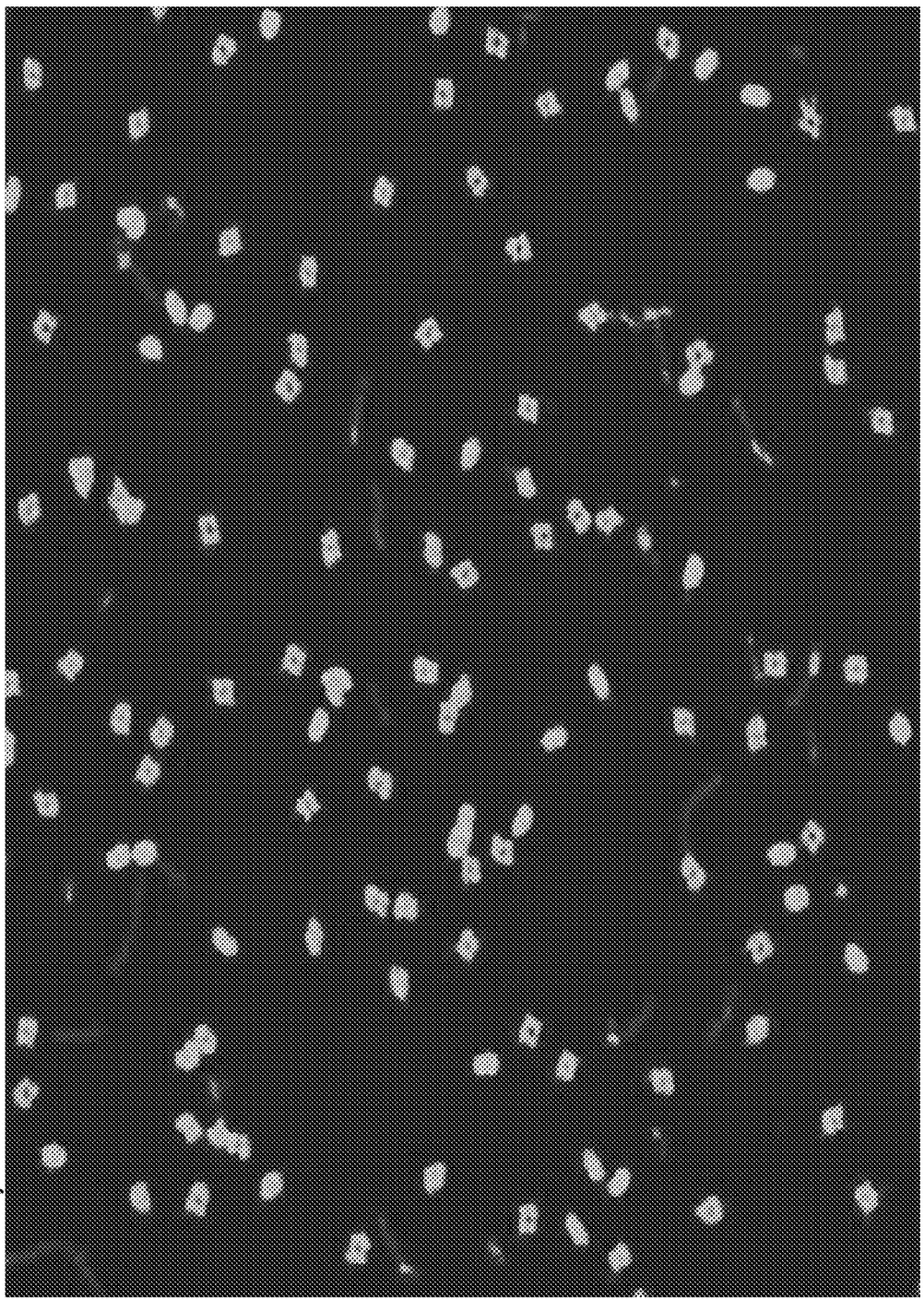
FIG. 6 demonstrates visualization of the square structures in FIG. 5.

FIG. 5 illustrates one example of a single RNA subunit having two kissing loops and two three-way junctions. In such a case, the kissing loops may be on the same side of the subunit structure, whereas in alternative cases the kissing loops may be on different sides of the RNA subunit (as in FIG. 1). In FIG. 5, the binding of one RNA subunit with another through interaction of their kissing loops generates a generally square structure (see FIG. 6).

FIG. 7A demonstrates RNA structures produced from RNA subunits having three kissing loops. Therein the structures produce a clearly resolved ladder from heterodimer and homodimer kissing. The image indicates that even with 1 y arm kissing, such a subunit is sufficient to form a ladder. Therefore, in specific embodiments when 2 arms are kissing such a structure is even more stable.

Figure 7B:
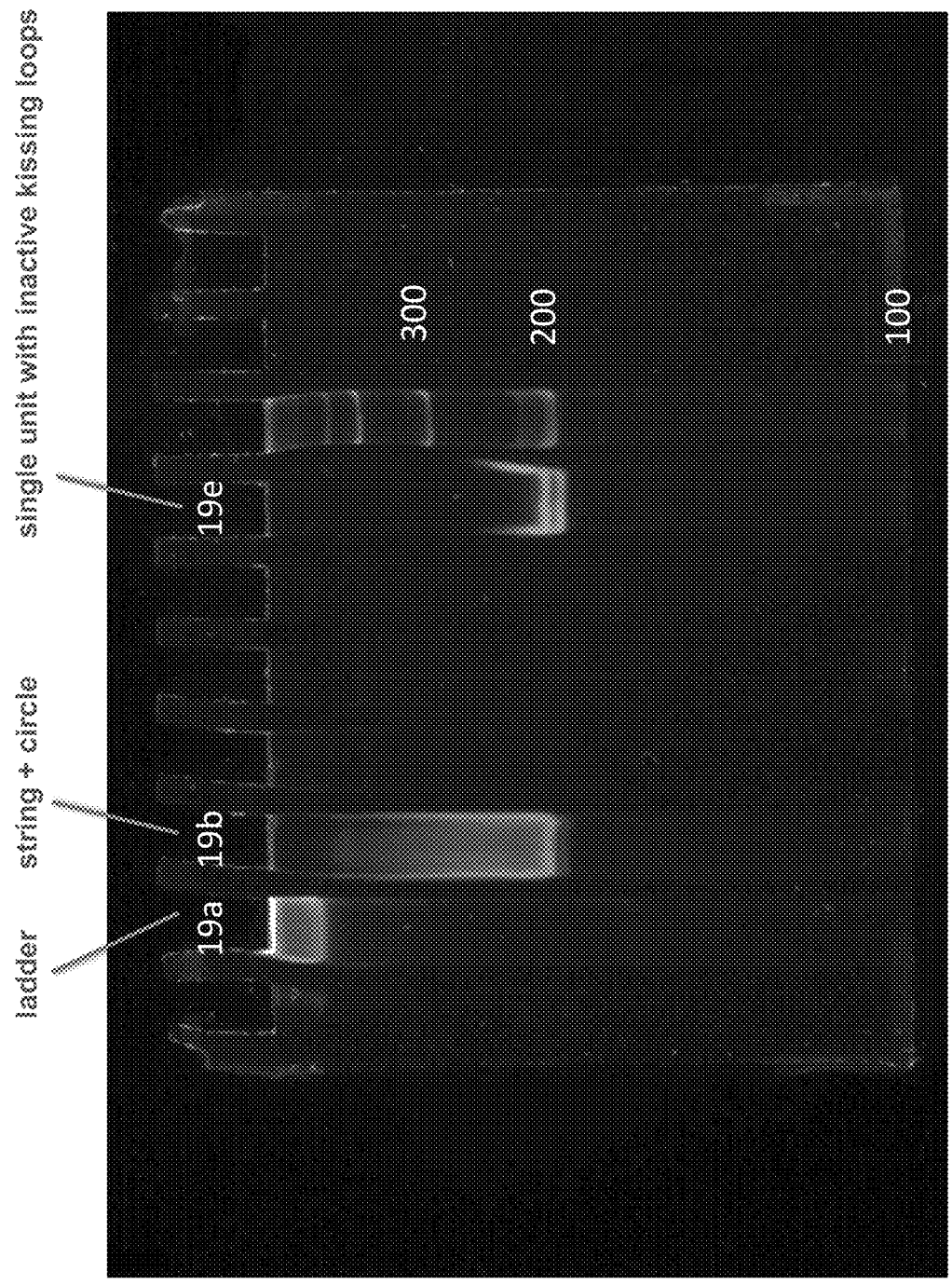

FIG. 7B demonstrates a non-denaturing RNA gel with samples of ladder structures, strings and circles, and a single unit with inactive kissing loops as a control. Because of their difference in molecular weight, single units migrate faster than assembly higher-order structures.

Figure 8A:
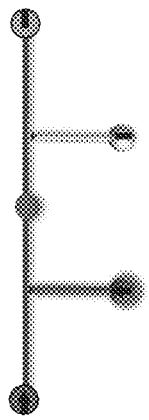

FIG. 8A demonstrates an example of a single RNA subunit comprising a generally bone shape and having an in-plane geometry with a Z arm. In this specific embodiment, the subunit has three three-way junctions and 4 kissing loops. Such a design permits polymerization of the RNA subunits in the X and partially Y direction.

FIG. 8B illustrates polymerization of such a subunit thereby generating a ladder having spaces between the "rungs" of alternating widths. In order to form an additional y kissing on one side only, in specific embodiments 4 activated KLs with both Y-axis arms pointing in the same direction were utilized. FIG. 9 further illustrates 1.5D ladder structures generated by such subunits that are the result of kissing between heterodimers and homodimers.

Figure 10:
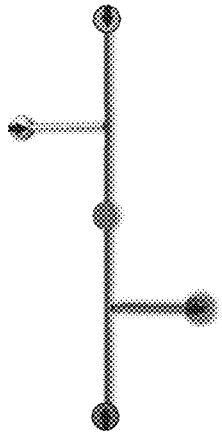
FIG. 10 provides illustration of a single RNA subunit having four kissing loops.

FIG. 10 illustrates an embodiment of an RNA subunit that is generally bone shaped having in-plane geometry and having a Z arm. In specific embodiments, the subunit comprises three three-way junctions and four kissing loops. Such an example of a RNA subunit structure allows for polymerization in both X and Y directions.

Figure 11:
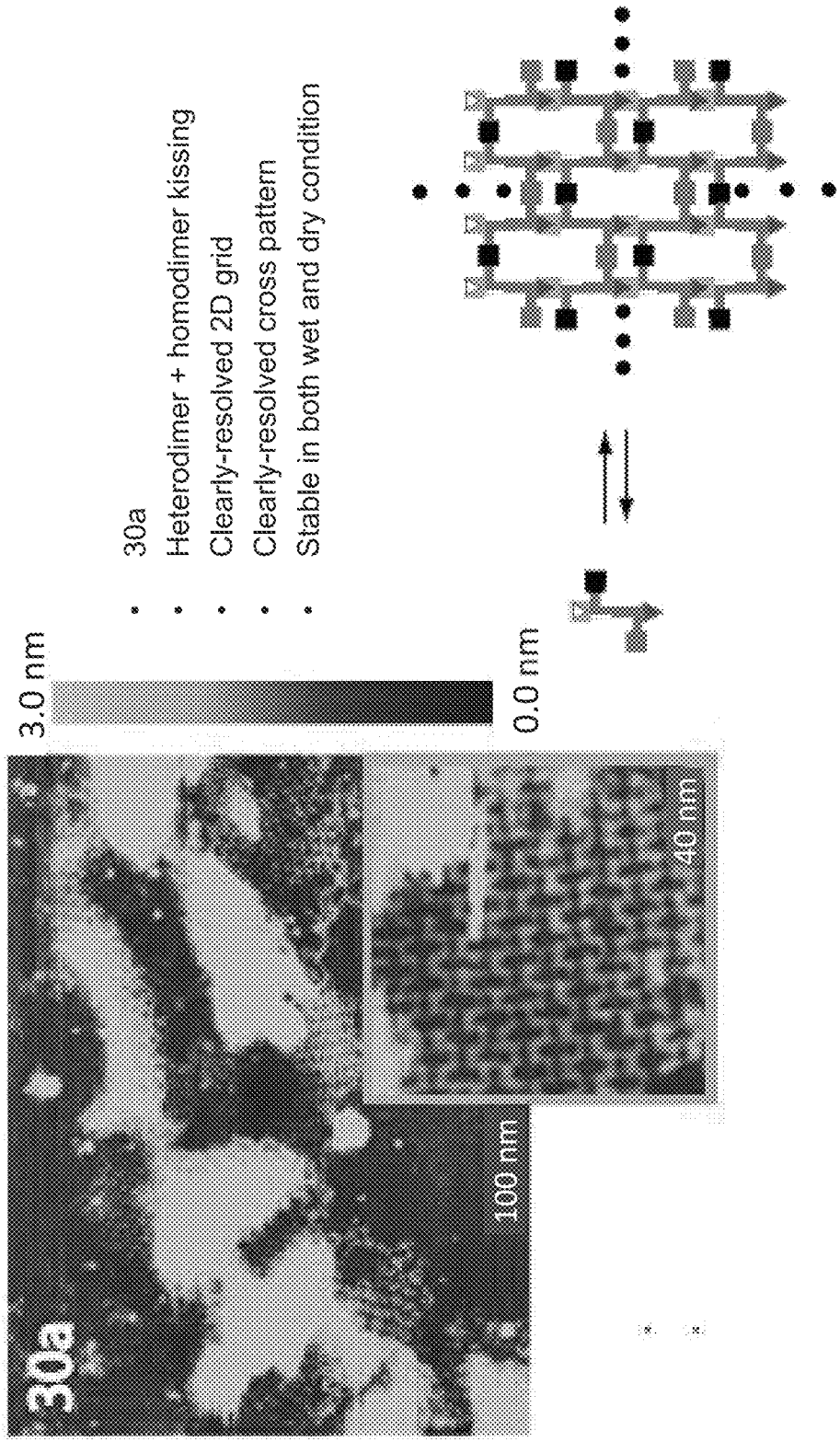
FIG. 11 provides a 2D grid with four kissing loops.
Figure 12:
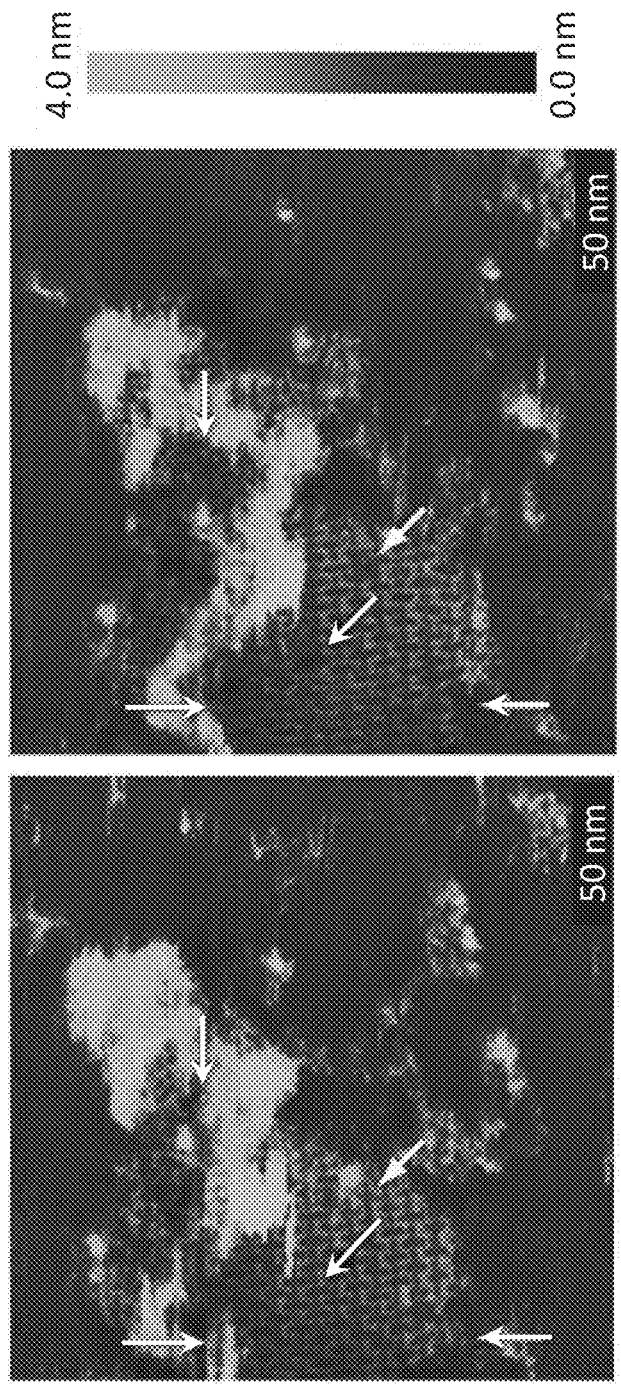
FIG. 12 demonstrates that the 2D grid is dynamic with constant remodeling.

FIG. 11 illustrates an example of a polymerized RNA structure from the subunit in FIG. 10 in which case there is kissing between heterodimers and homodimers. The structure generally has a 2D grid pattern. In such an embodiment, an extended Y axis is utilized. FIG. 12 demonstrates that the particular 2D grid is dynamic with constant remodeling.

Figure 13:
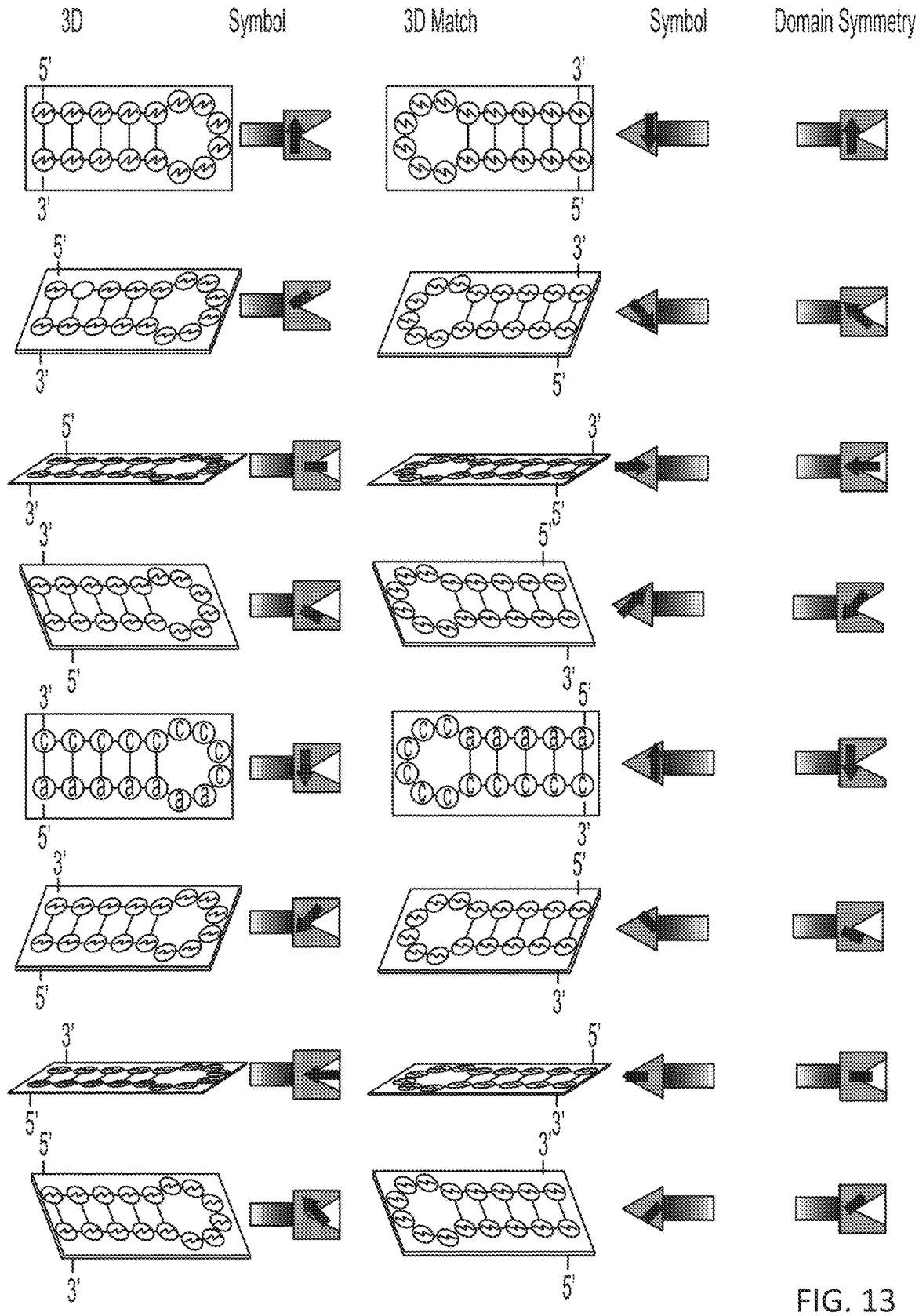
FIG. 13 shows an effect of kissing loop twists. Figure discloses SEQ ID NOS 11 and 12.
Figure 13:
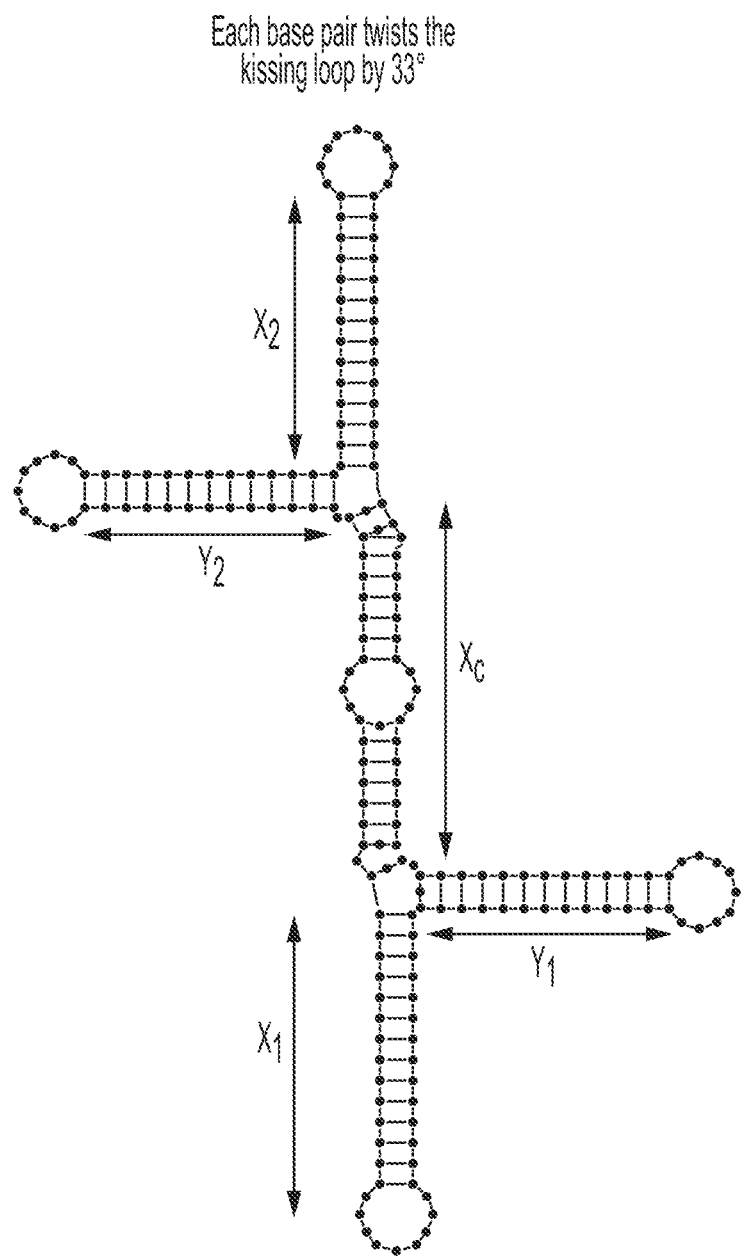
Figure 14:
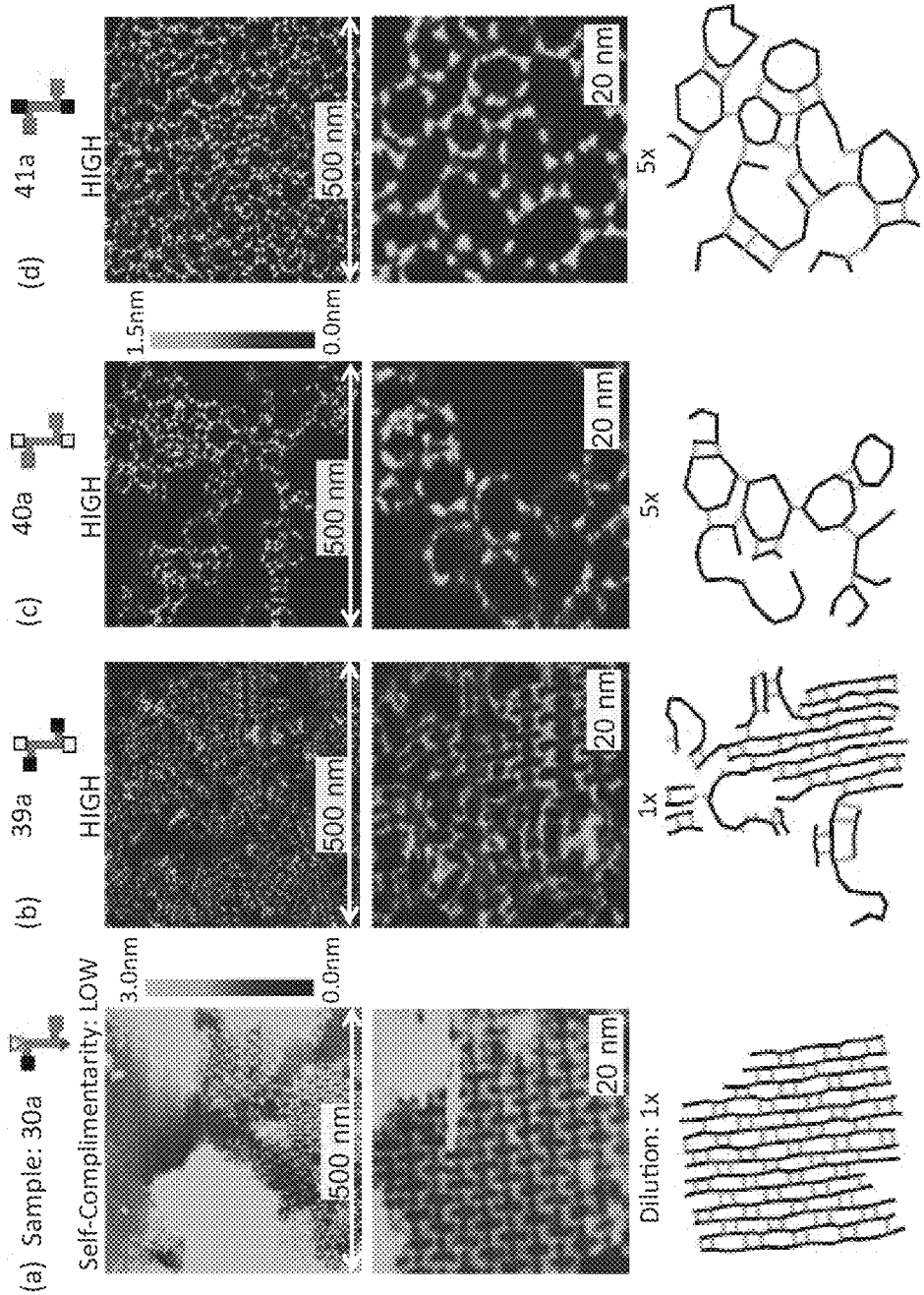
FIG. 14 demonstrates that turning kissing loops leads to chain-loop structures.

FIG. 13 demonstrates the effect of kissing loop twists. Adding each base pair in the arm twists the kissing loop by approximately 33°. This allows fine-tuning of the shape of assembled structures. FIG. 14 shows that turning the kissing loops leads to chain-loop structures. As shown therein, a variety of subunits having a variety of self-complimentarity results in different structures.

Figure 15:
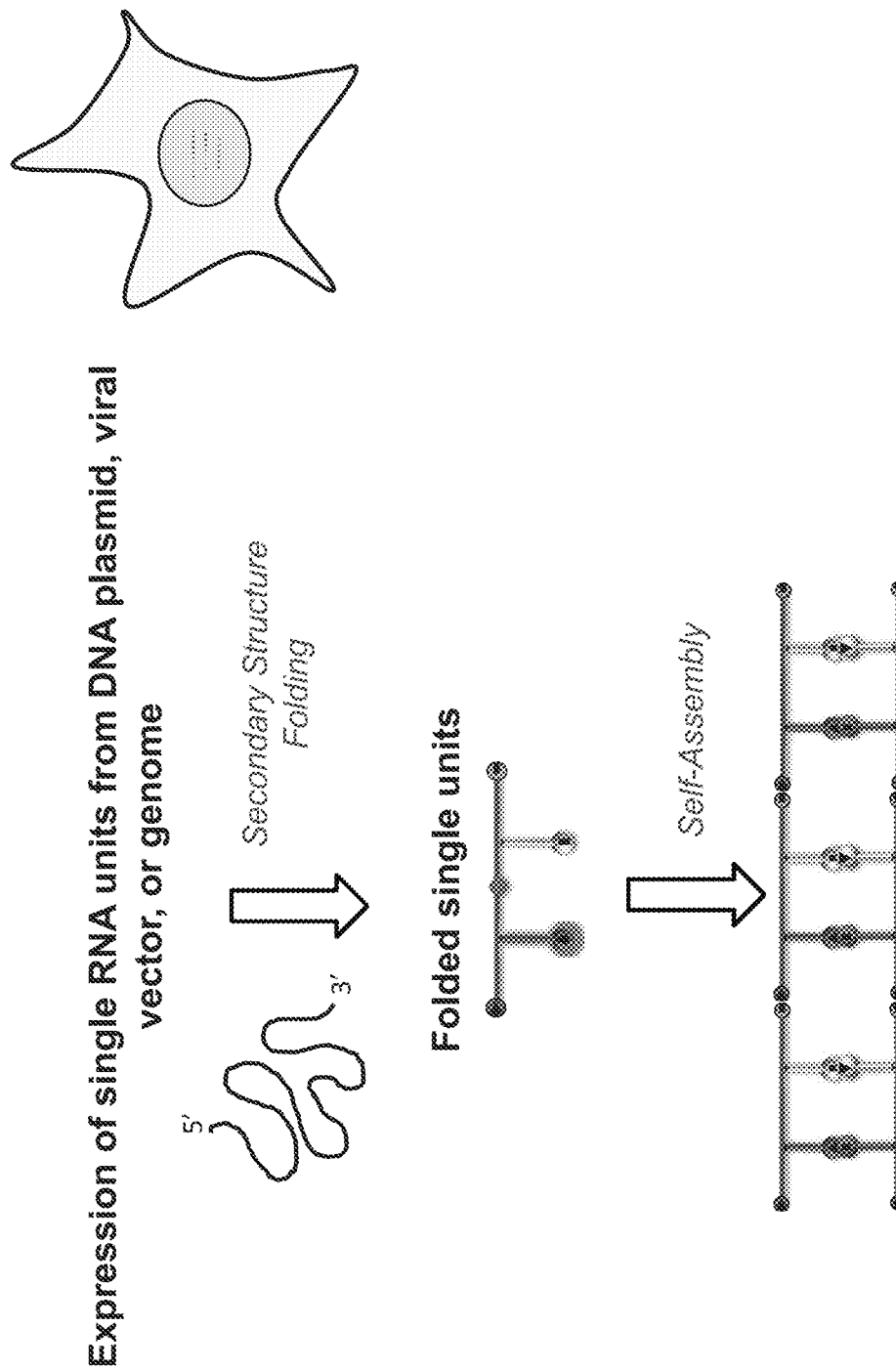
FIG. 15 provides a schematic wherein ssRNA molecules are produced in cells that then self-assemble to produce the RNA structures.

In particular embodiments, RNA structures are produced in a cell. The cell may be of any kind. The cell may be transformed or transfected with ssRNA that upon secondary structure folding produces folded single RNA subunits that then within the cell self-assemble into polymerized structures (FIG. 15). An expression vector (viral or plasmid, for example) comprising sequence that is expressible into RNA may be introduced into cells (such as human 293T or U2OS cells for example). The expression unit can be inserted in the genome as a permanent fixture of the genome. Upon expression in the cells, the RNA structures may be analyzed for their presence as structures, for example by gel shifting assays (FIG. 7B) or Northern blot. As shown in FIG. 16, single RNA subunits are expressed in human cells and subsequently RNA from the cell is analyzed, such as by Northern blot. If the kissing loops are engaged, the RNA is stable and detectable on an Northern RNA gel. If the kissing loops are inactive as a control, no band appears on the gel.

Figure 17:
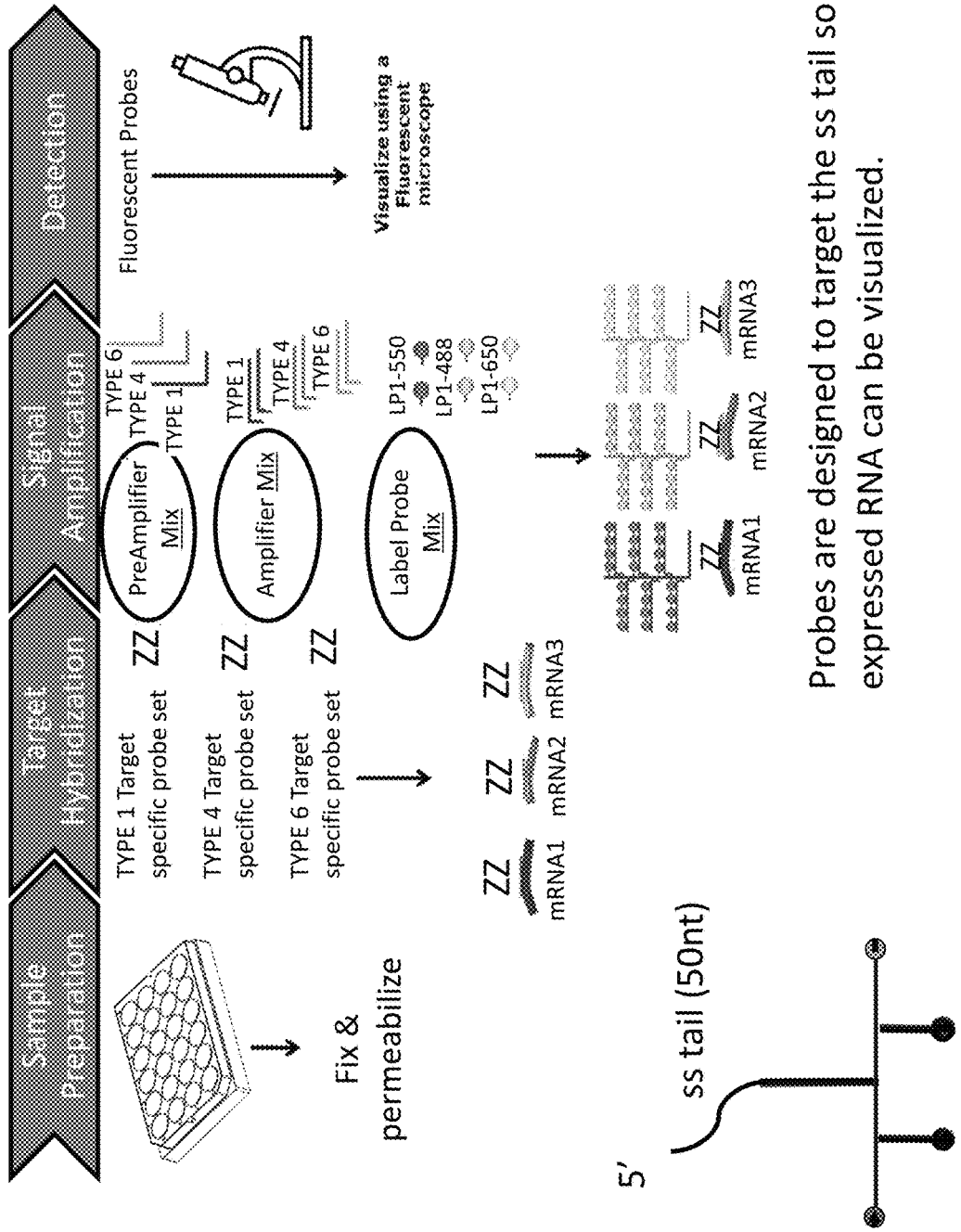
FIG. 17 shows one embodiment for visualization of nanostructures in cells using RNA FISH.
Figure 18A:
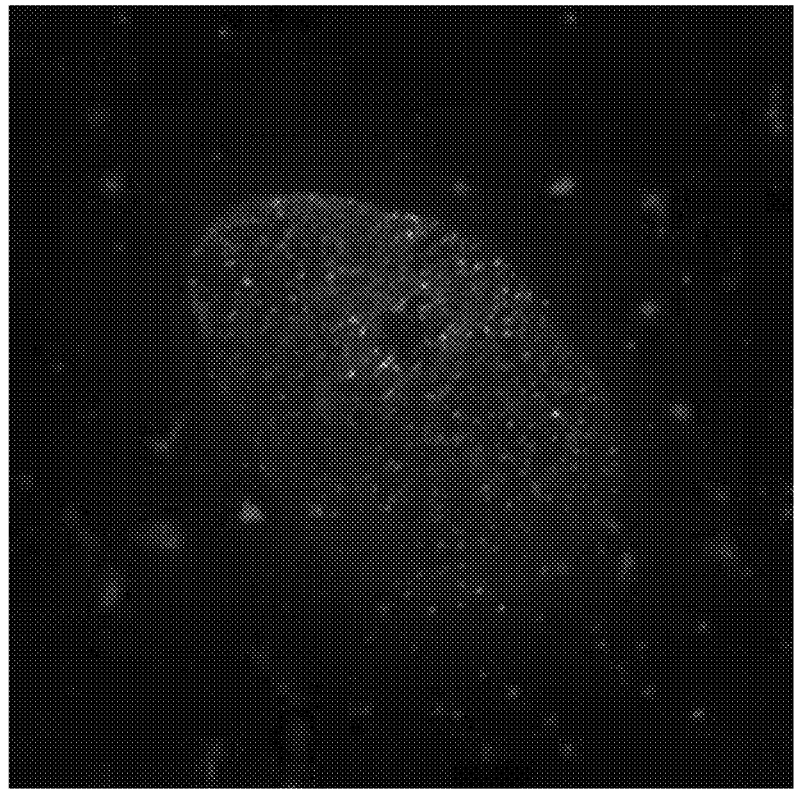
FIGS. 18A and 18B.
Figure 18B:
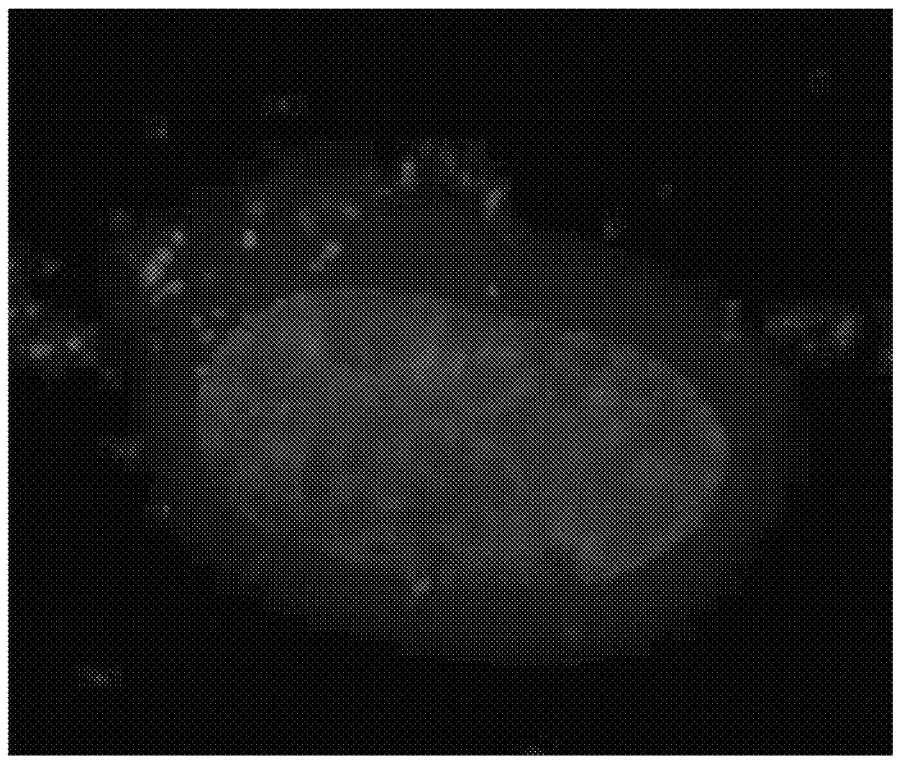
Figure 20:
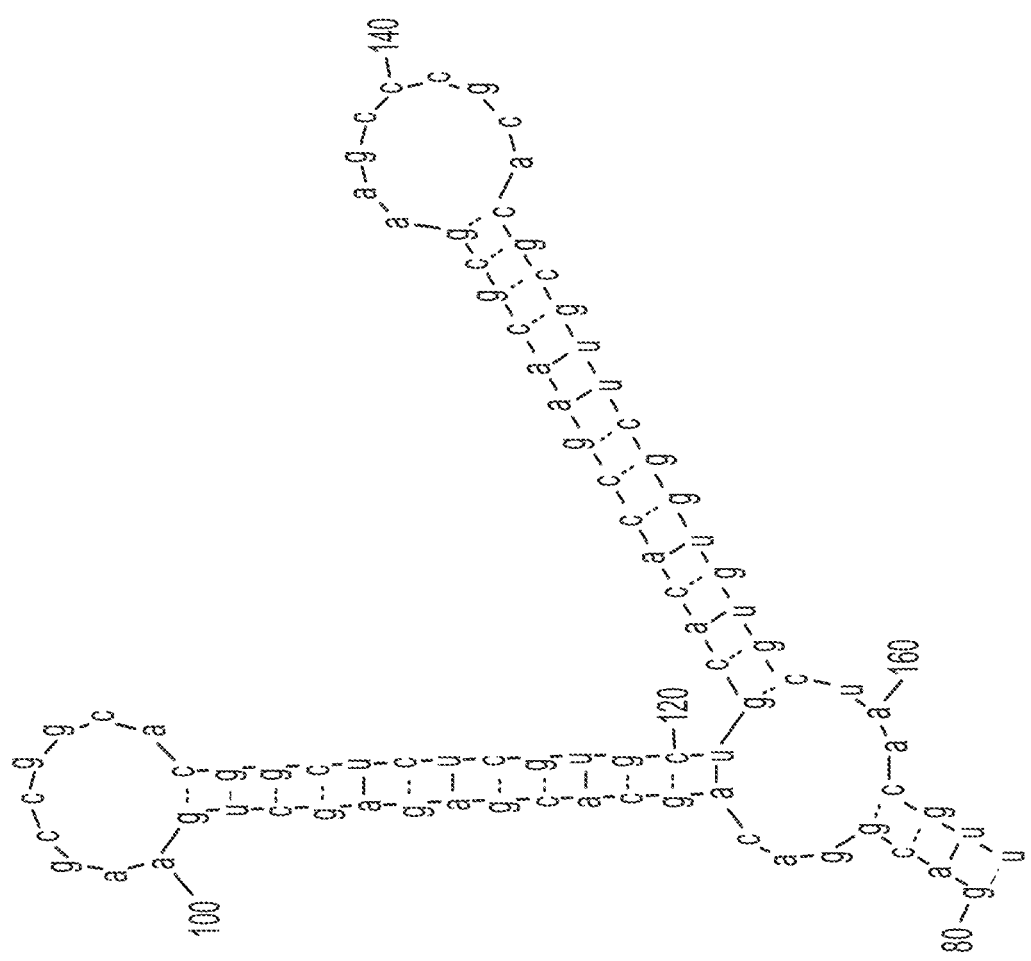
FIG. 20 provides an example of a specific RNA subunit (3wj-19f) having three kissing loops and two three-way junctions. (SEQ ID NO:1)
Figure 20:
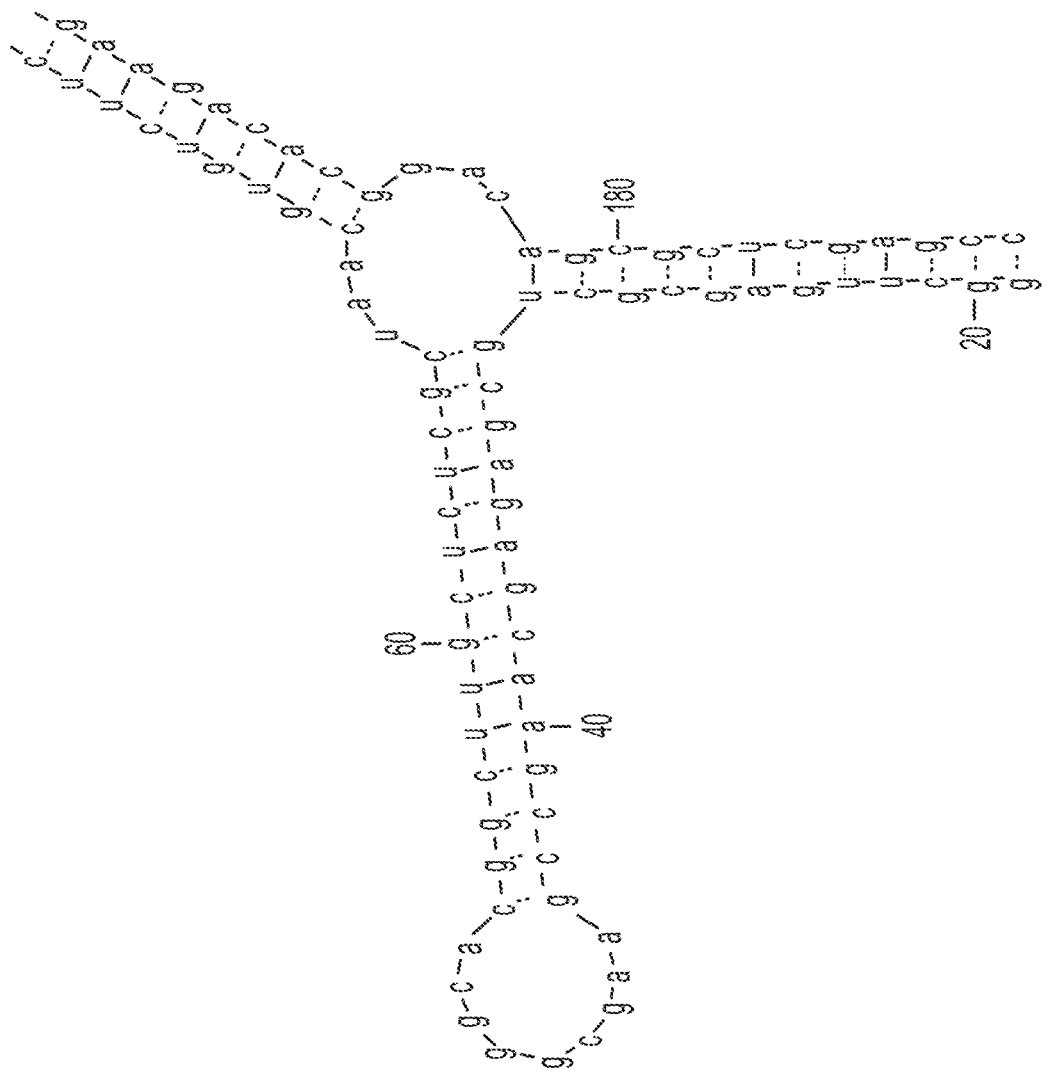
Figure 20:
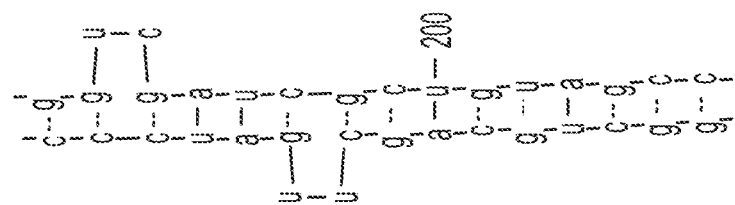
Figure 21:
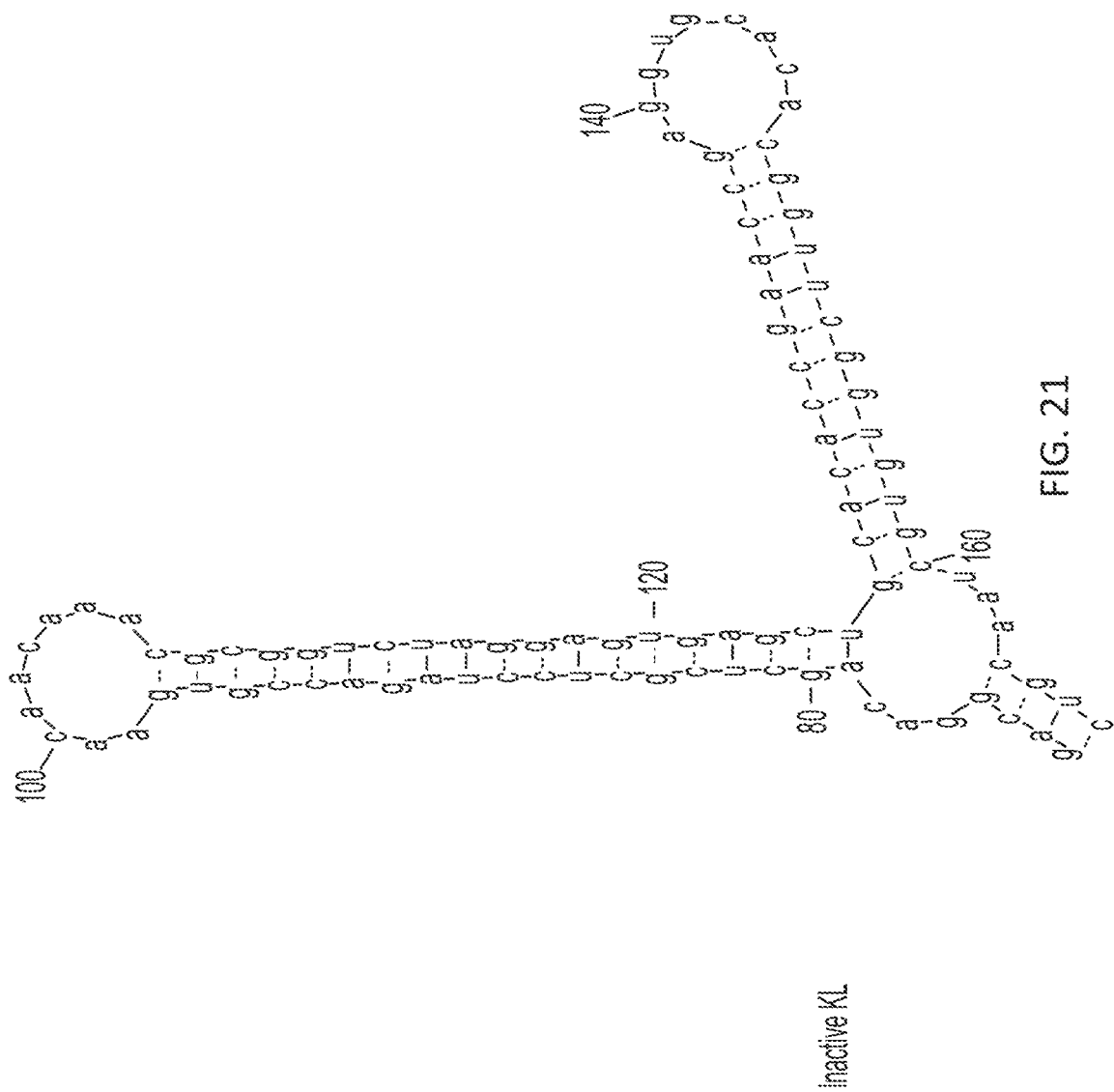
FIG. 21 provides an example of a specific RNA subunit (3WJ-22b) having four kissing loops and three three-way junctions. (SEQ ID NO:2)
Figure 21:
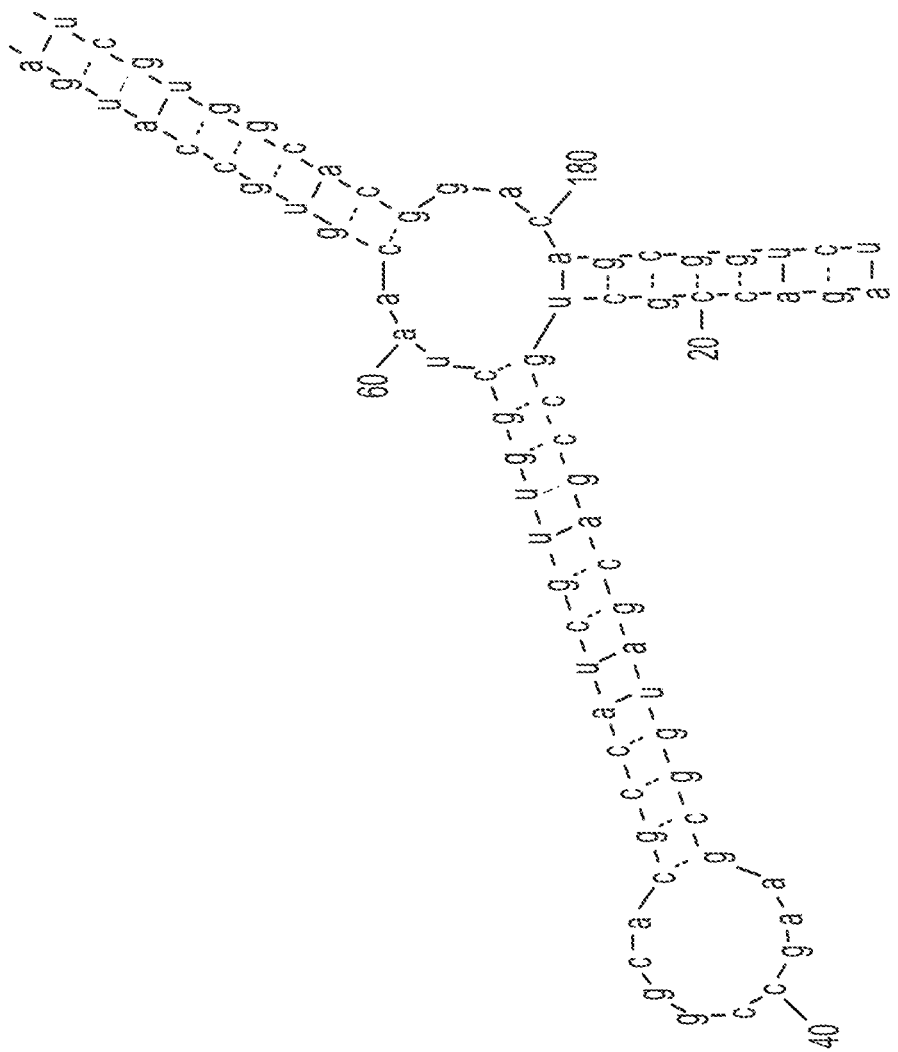
Figure 22:
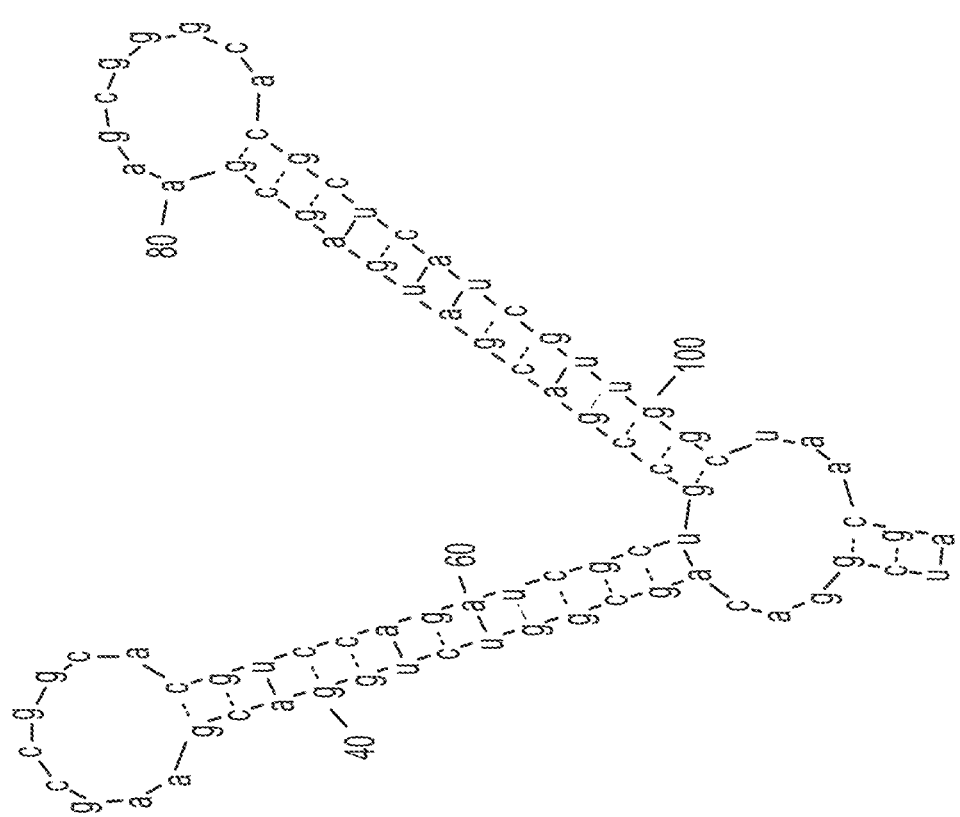
FIG. 22 illustrates an example of a specific RNA subunit (3wj-24a) having an inactive Y kissing loop and two three-way junctions. (SEQ ID NO:13)
Figure 22:
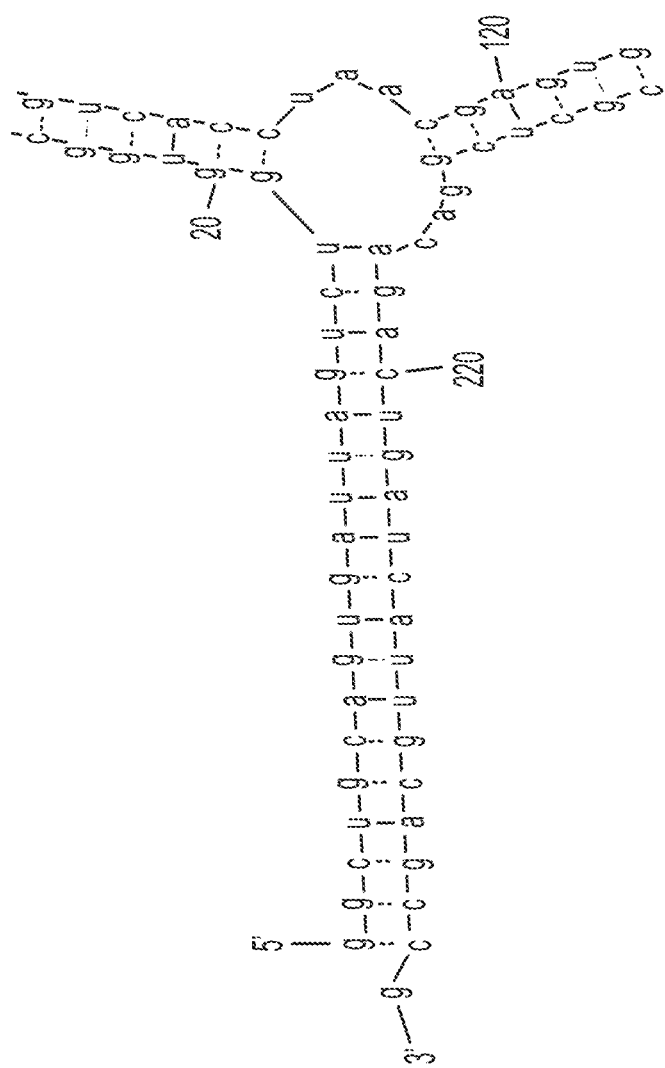
Figure 22:
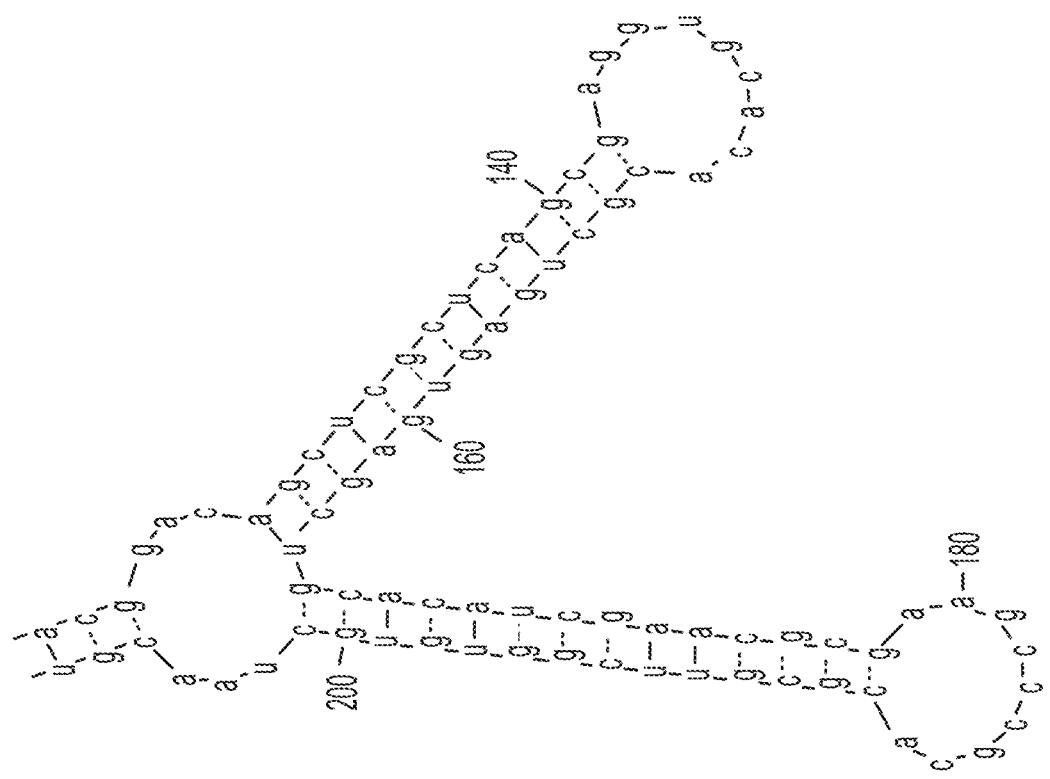
Figure 23:
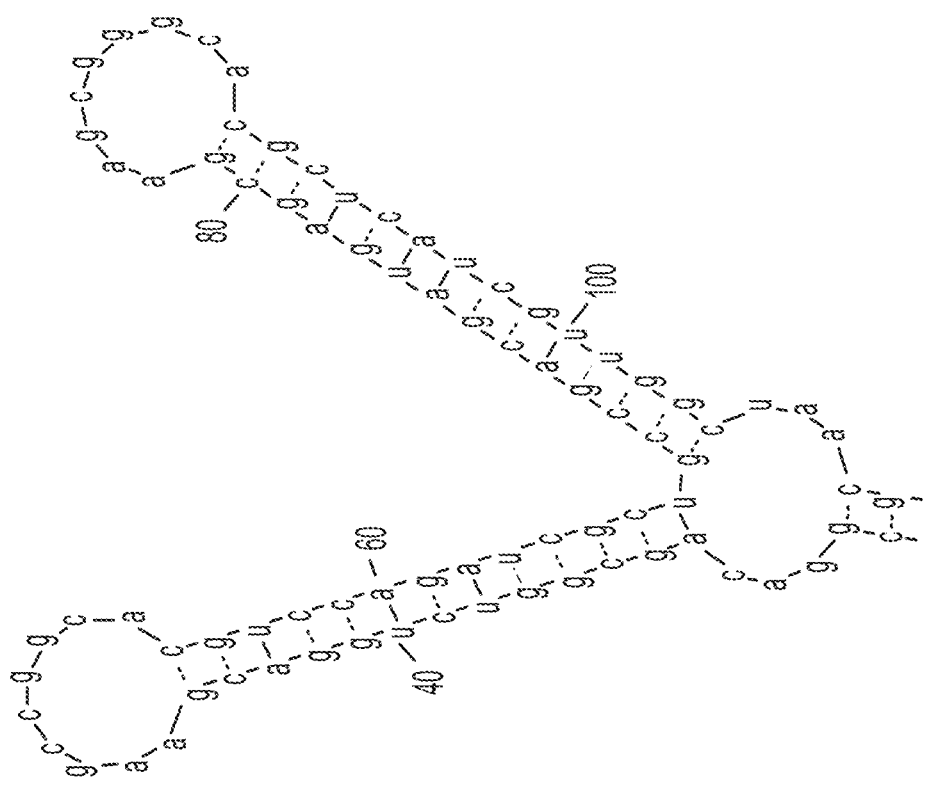
FIG. 23 shows an example of a specific RNA subunit (3WJ-28a) having four kissing loops and three three-way junctions. (SEQ ID NO:14)
Figure 23:
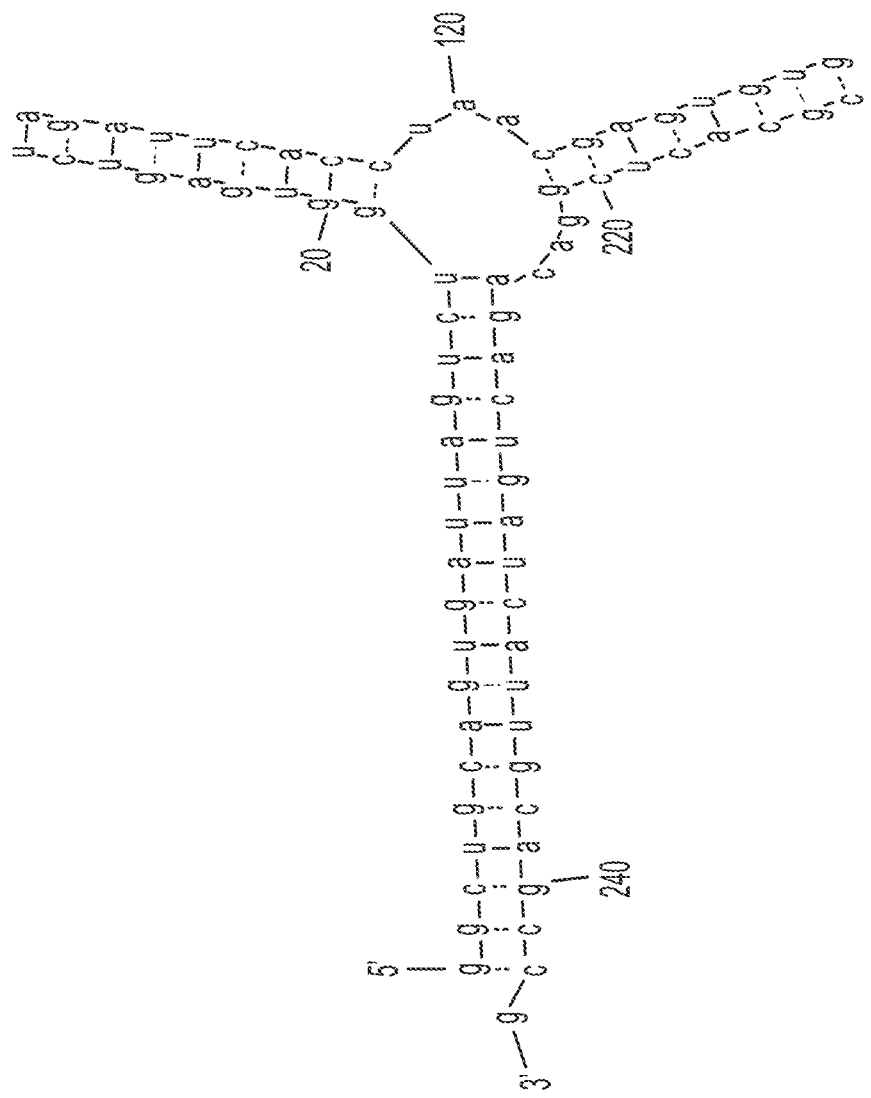
Figure 23:
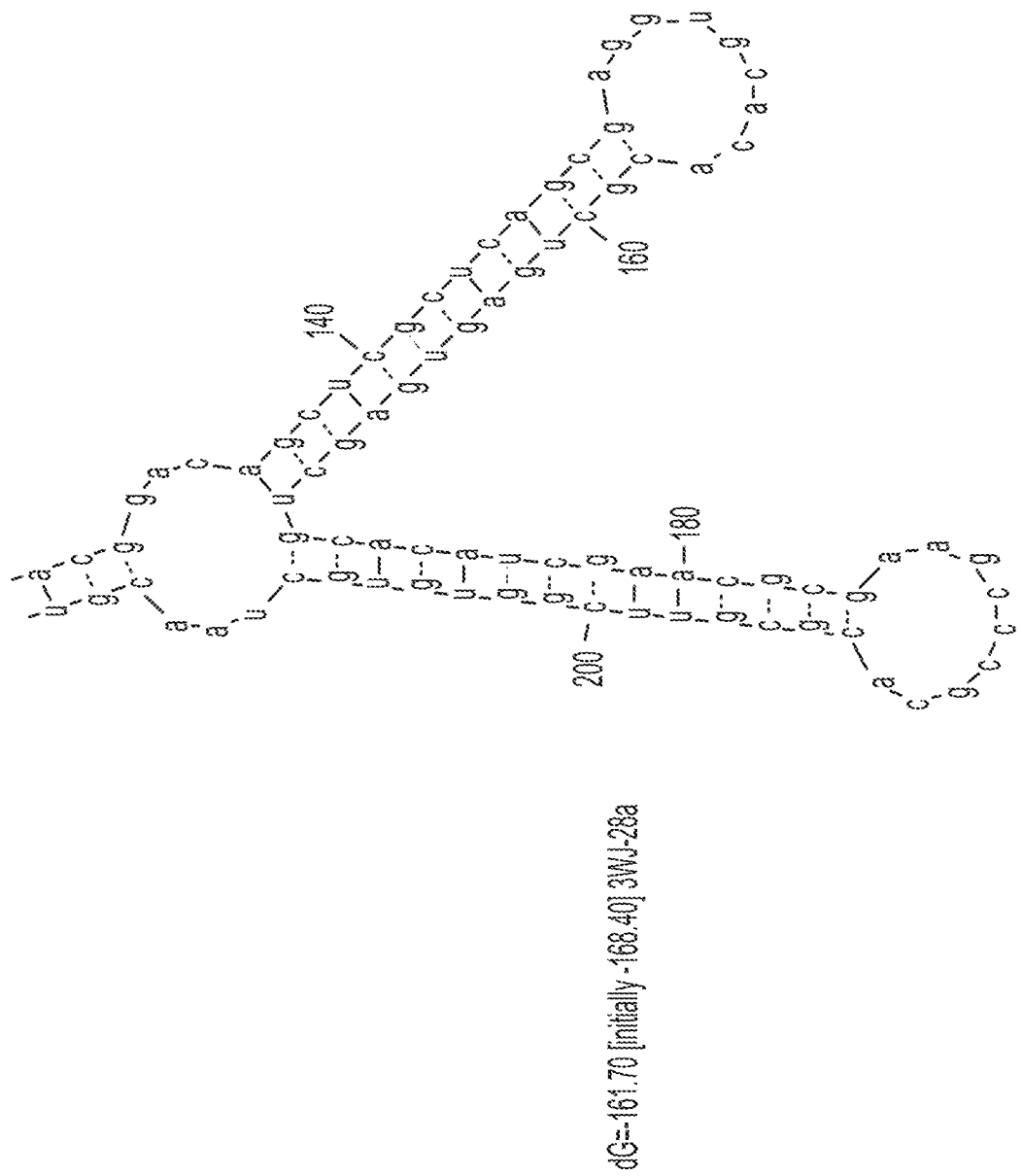
Figure 24:
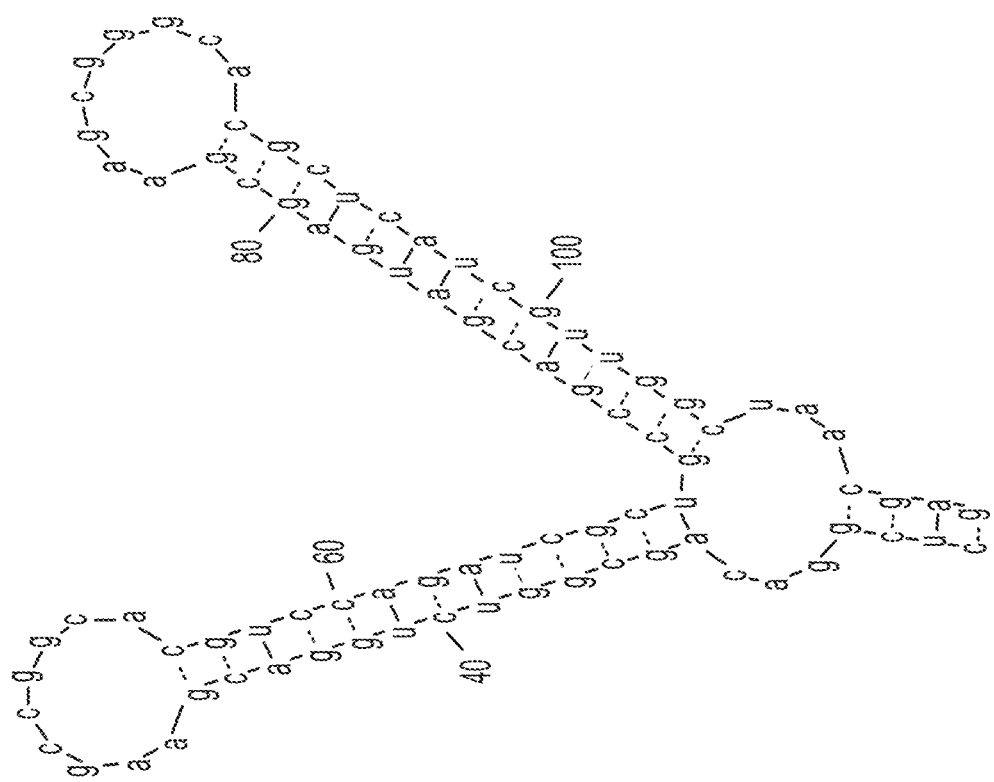
FIG. 24 provides an example of a specific RNA subunit (3WJ-30a) having four kissing loops and three three-way junctions. (SEQ ID NO:15)
Figure 24:
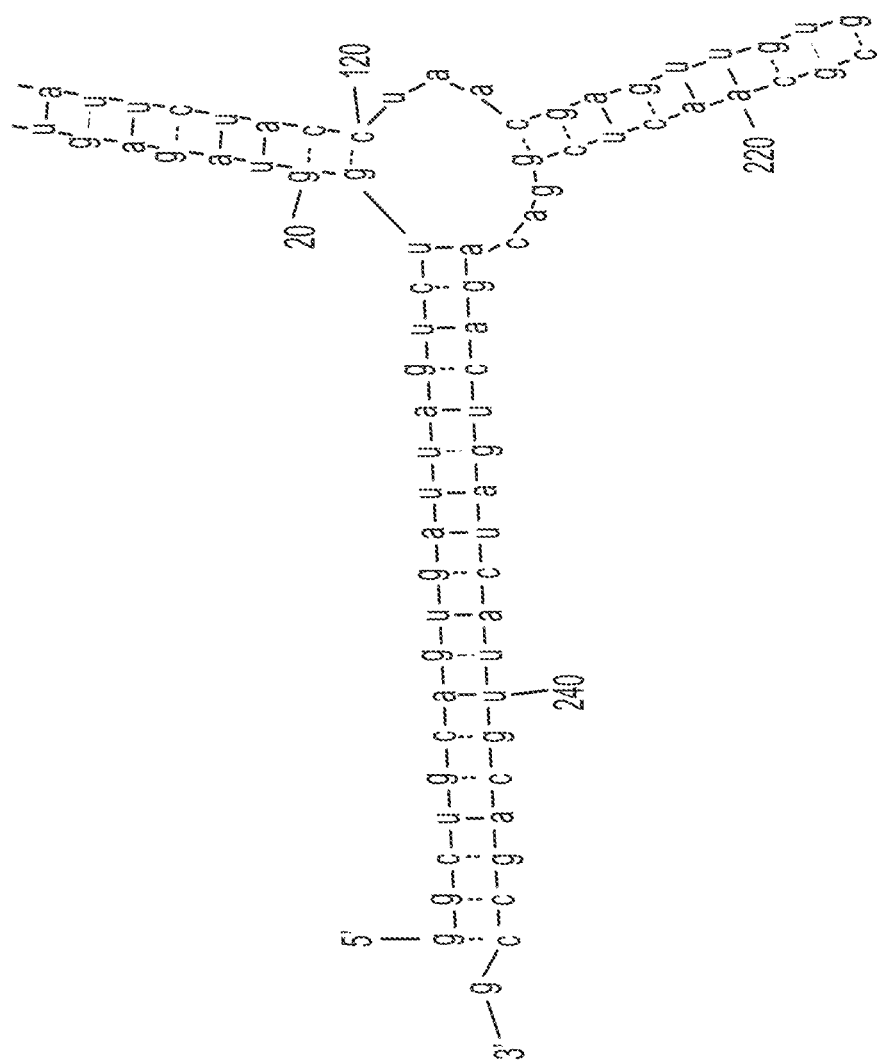
Figure 24:
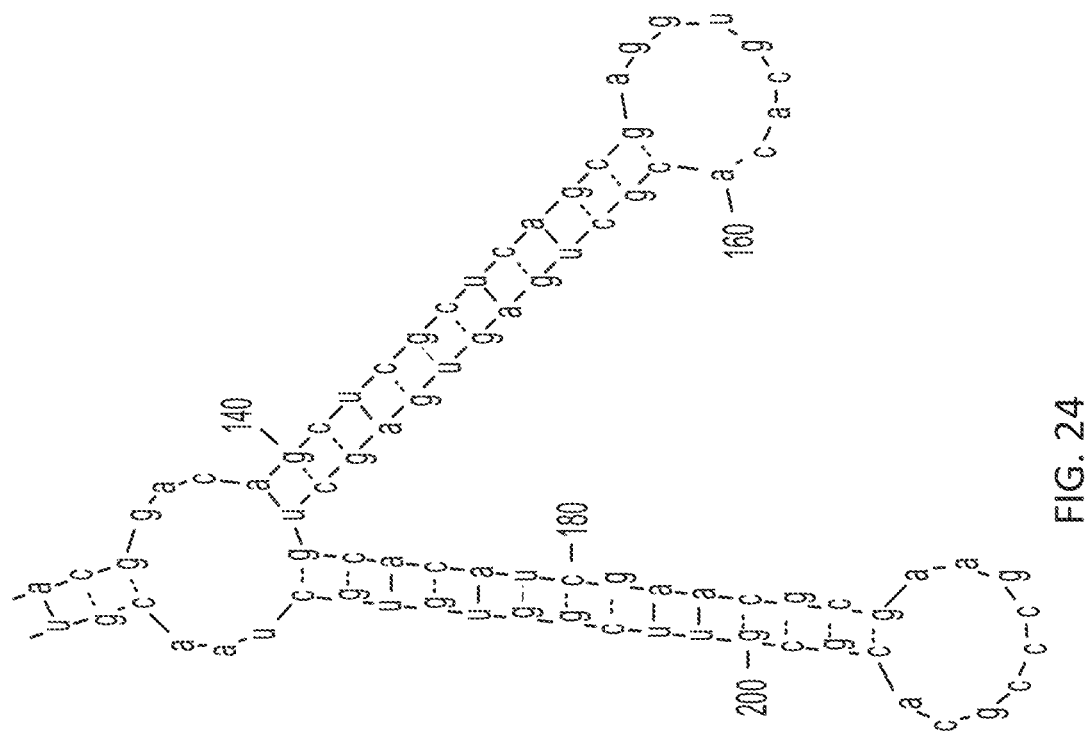
Figure 25:
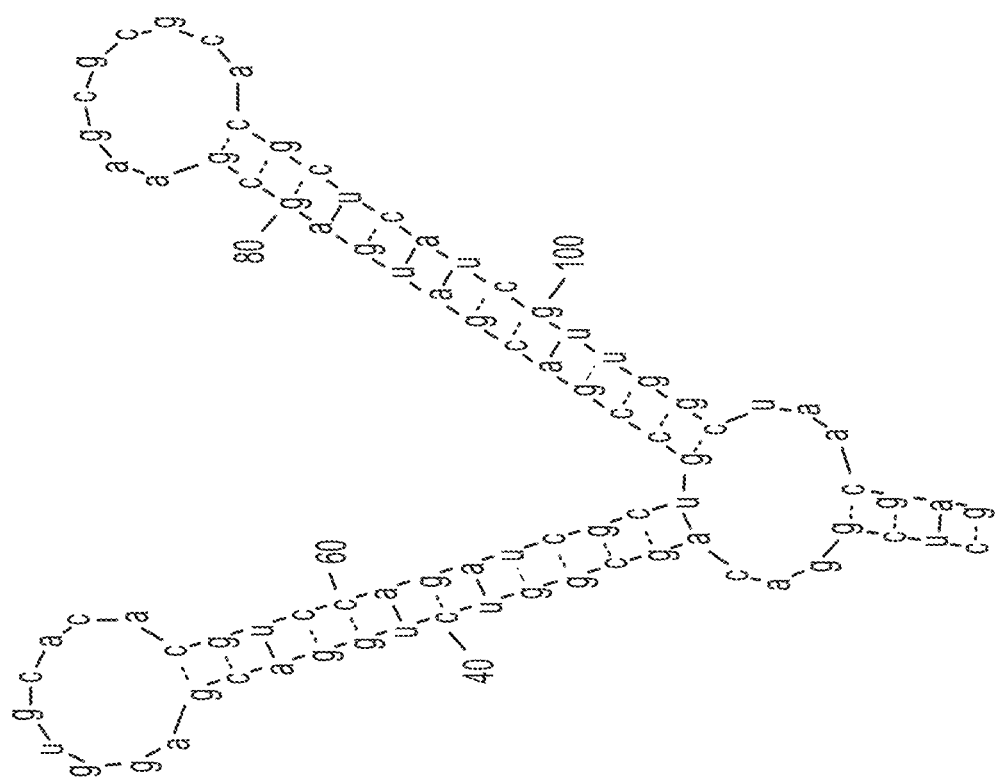
FIG. 25 shows an example of a specific RNA subunit (3wj-39a) having four kissing loops and three three-way junctions. (SEQ ID NO:16)
Figure 25:
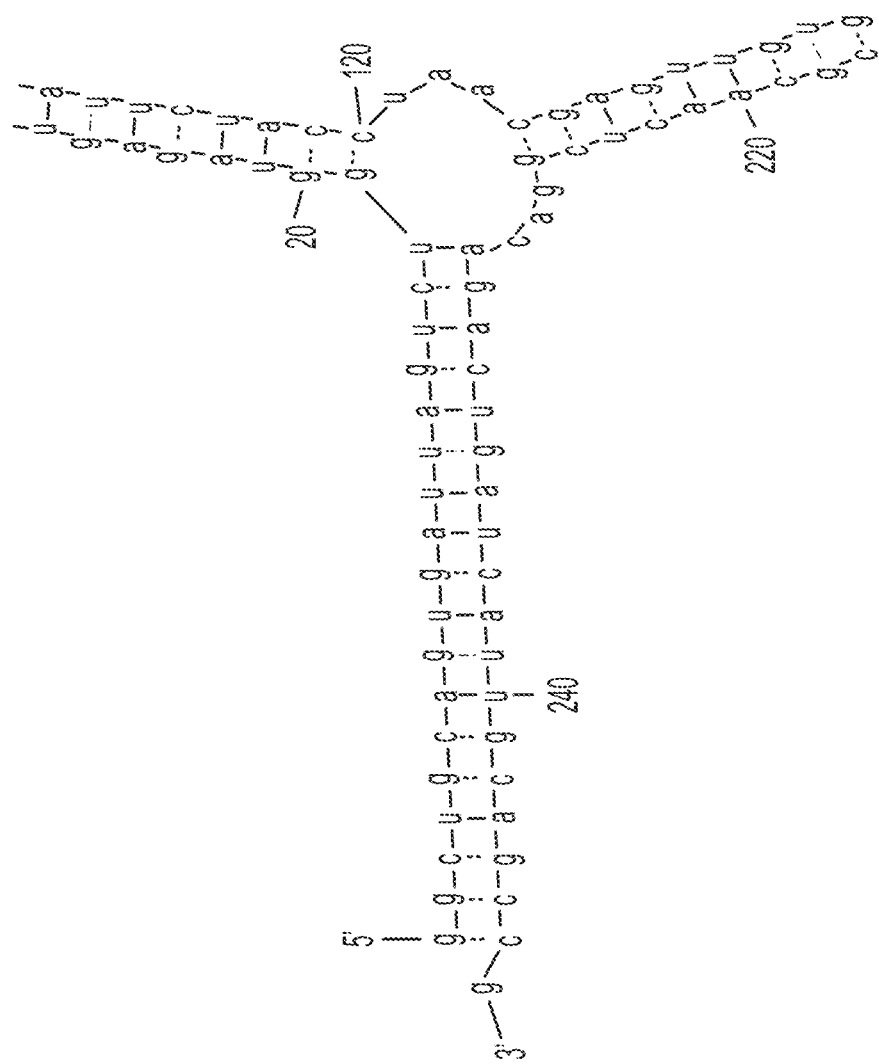
Figure 25:
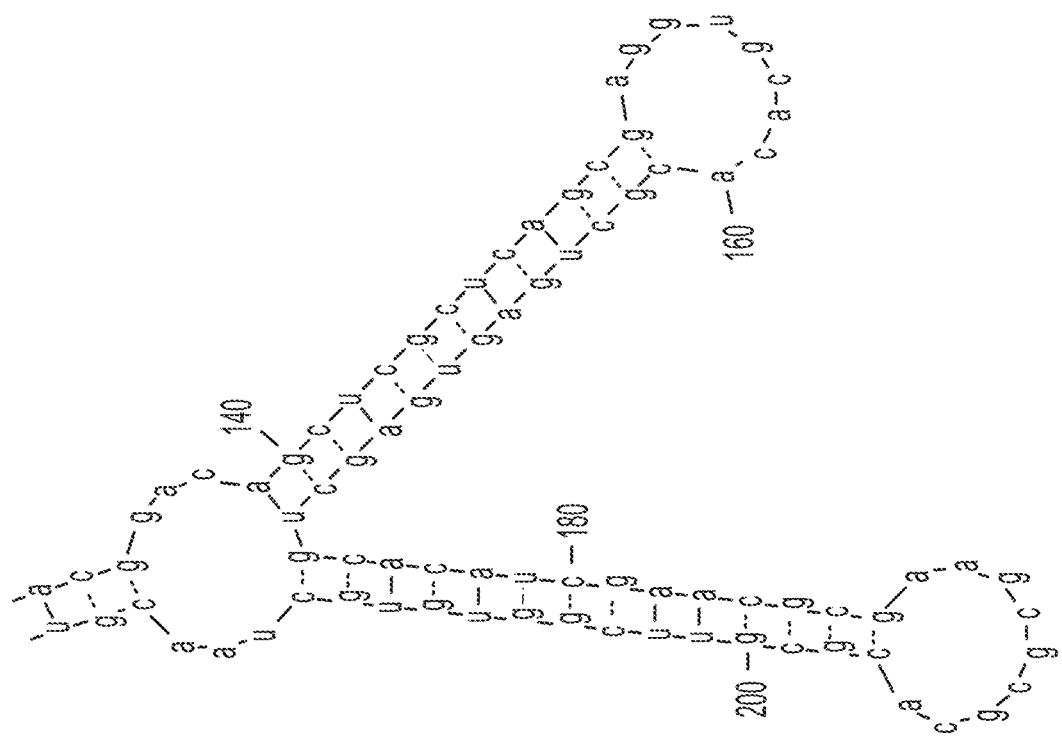
Figure 26:
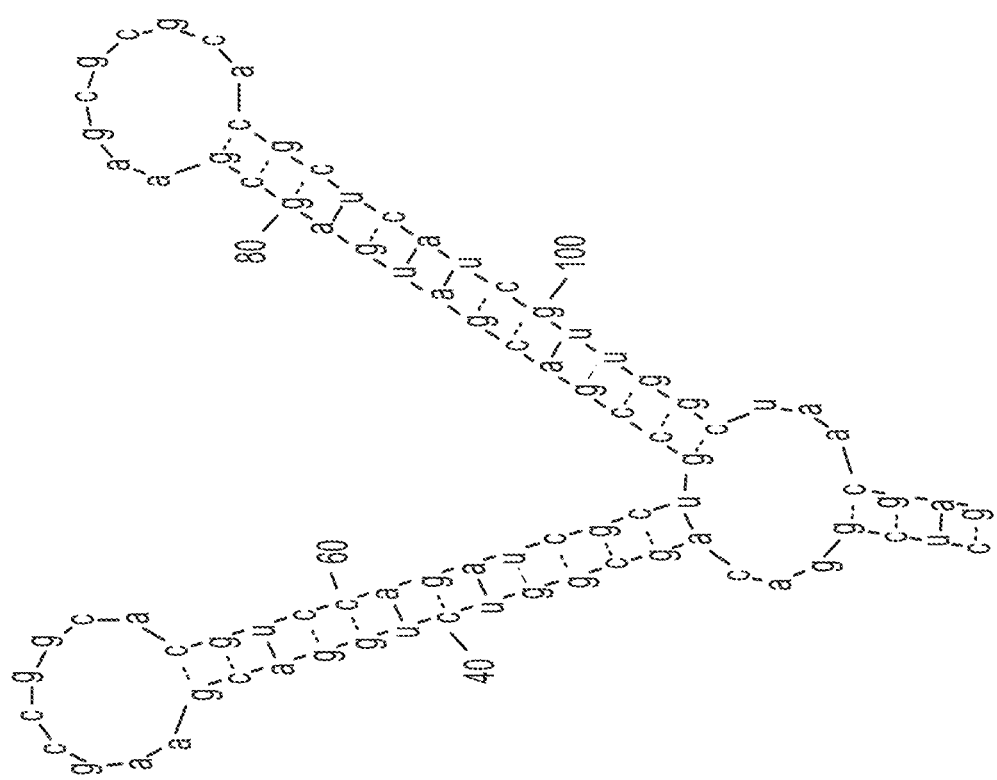
FIG. 26 illustrates an example of a specific RNA subunit (3WJ-40a) having four kissing loops and three three-way junctions. (SEQ ID NO:17)
Figure 26:
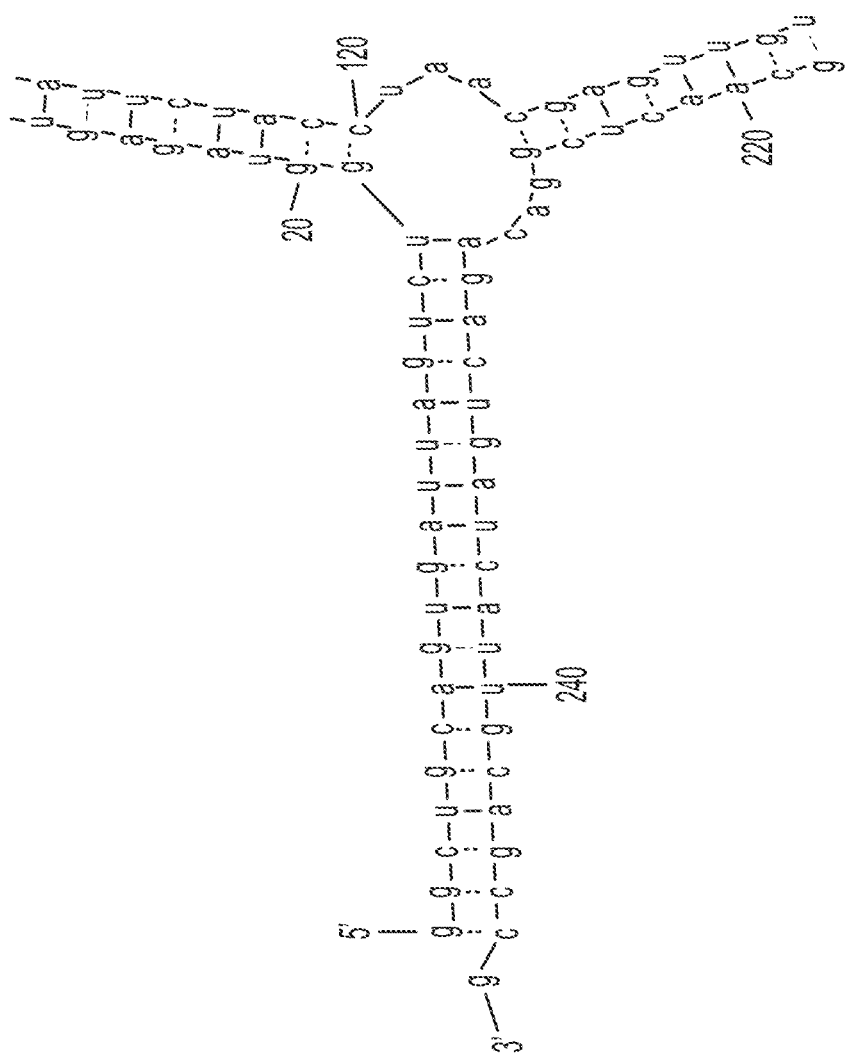
Figure 26:
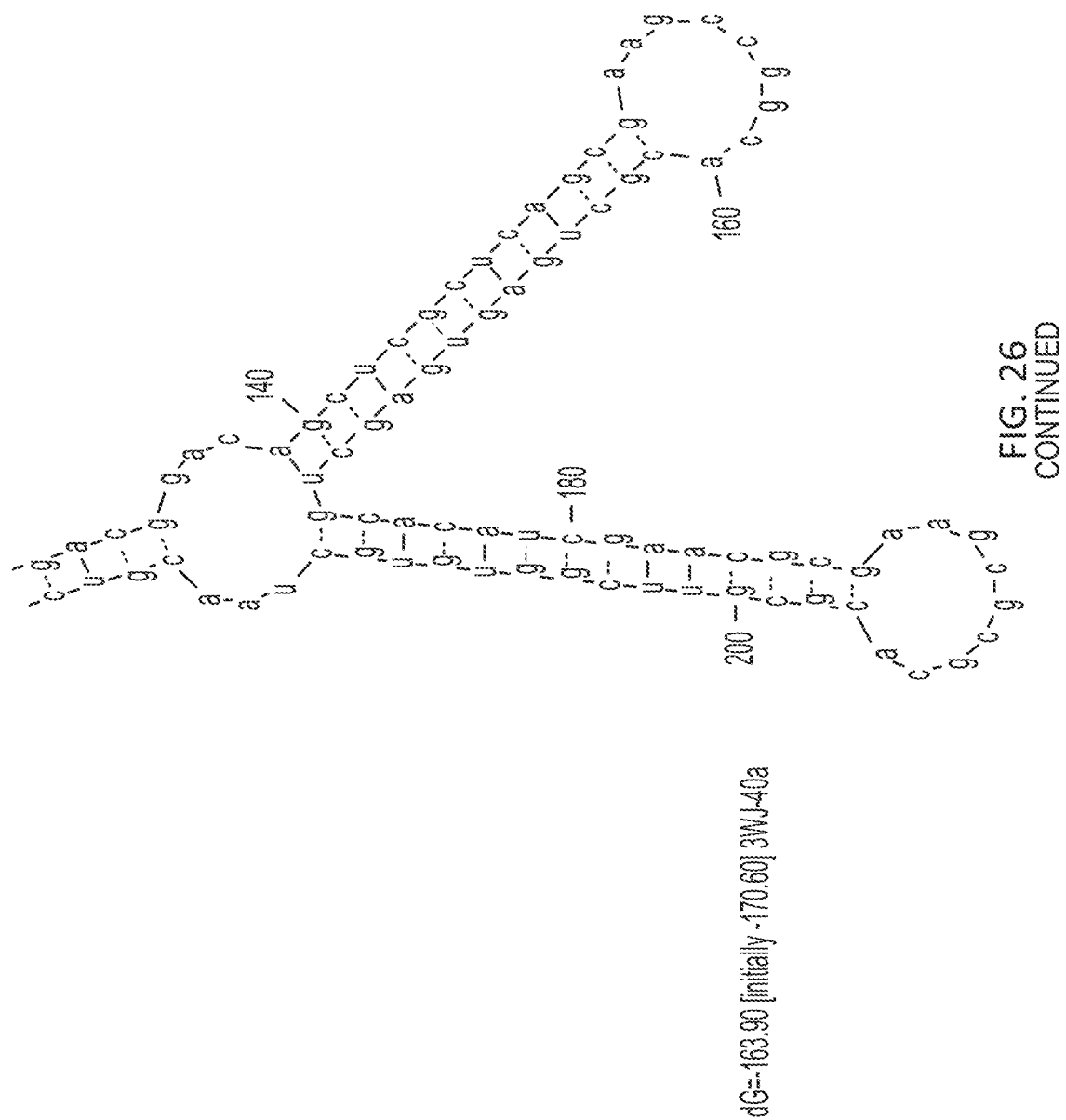
Figure 27:
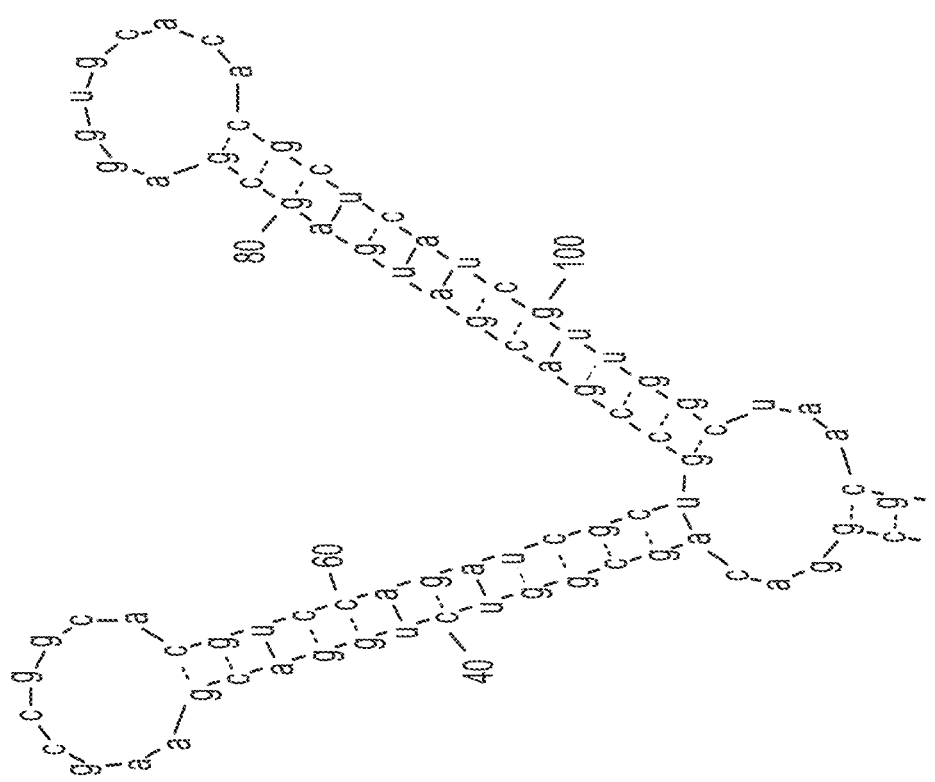
FIG. 27 shows an example of a specific RNA subunit (3WJ-41a) having four kissing loops and three three-way junctions. (SEQ ID NO:18)
Figure 27:
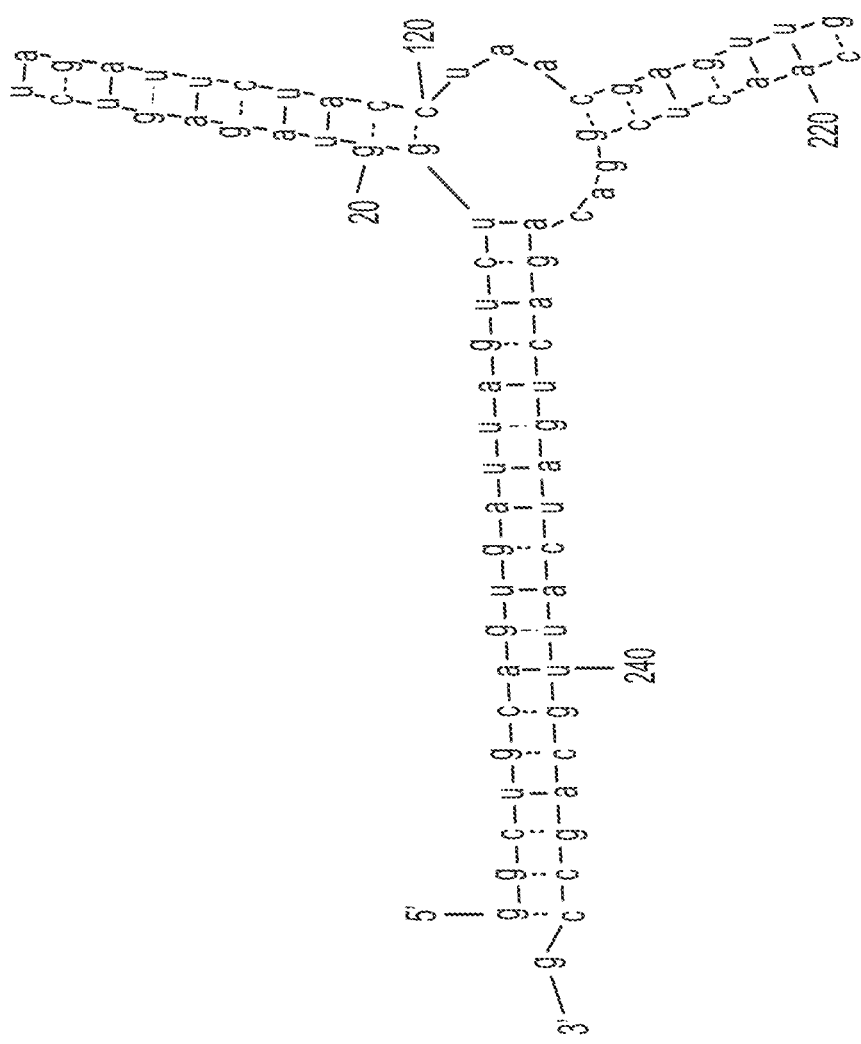
Figure 27:
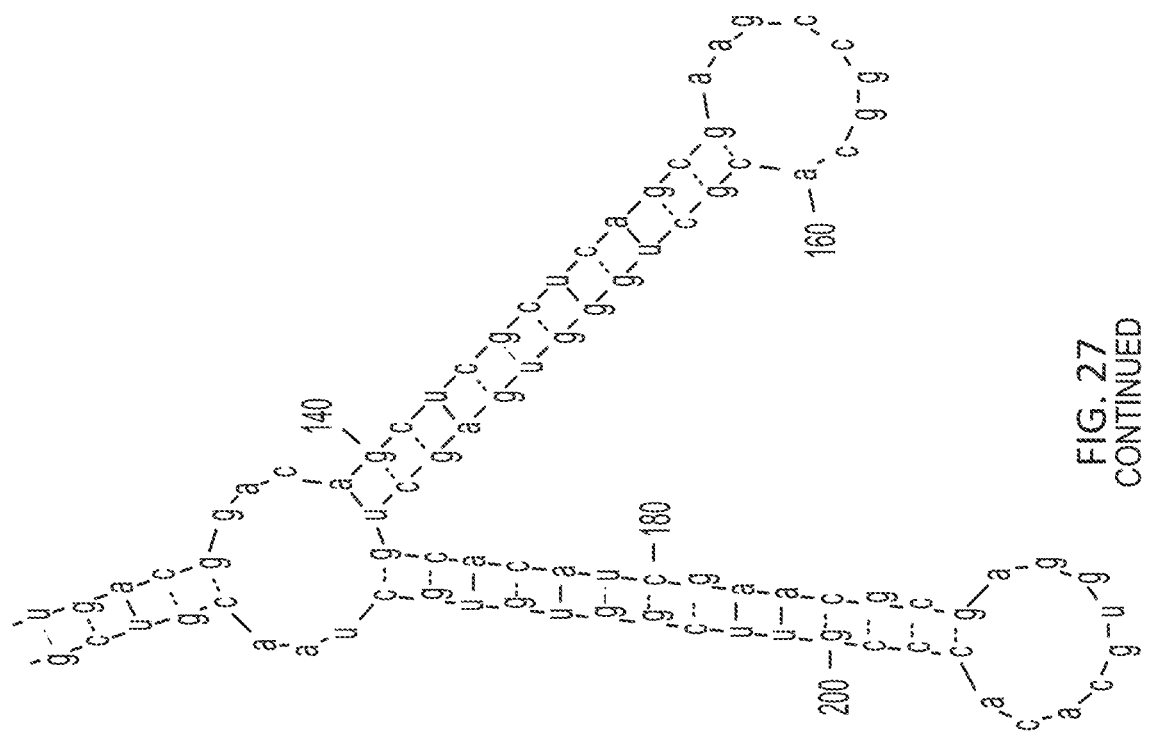

In particular embodiments, one can visualize nanostructures in cells, for example using RNA FISH combined with light microscopy. As illustrated in FIG. 17, one can utilize ssRNA tails on the RNA subunits and the ss tail can be the target of a labeled probe that allows detection of the subunits or RNA polymers comprising the RNA subunits. The label may be of any kind, including fluorescent, radioactive, or colorimetric, for example. FIG. 18A shows detection of a structure as an example with active kissing loops and FIG. 18B as a control lacking active kissing loops. The resolution of light microscope however has a limit. The fine structure of assembled RNA at nanometer resolution can be confirmed by AFM analysis of extracted RNA from cells.

In some embodiments, an RNA molecule or one or more RNA molecules in a plurality thereof comprises at least one arm that extends from a three way junction away from a plane that comprises two arms from the same junction (the extending arm may be referred to as the Z arm). In specific embodiments, the Z arm protects the 5' and/or 3' end of the RNA molecule. In such a case, the part of the RNA molecule that has activity is in the XY plane.

However, in some cases, a RNA molecule can host additional three way junctions and kissing loops in the Z-axis. This modularity or flexibility allows the possibility of polymerization in the Z direction for constructing higher order structures with 3-dimension.

II. Applications for RNA Structured Compositions

In one embodiment, the RNA structures produced by methods encompassed by the disclosure are utilized for a specific purpose. In particular embodiments, genetically encodable higher order RNA nanostructures are utilized for synthetic biology applications in cells, including mammalian cells.

The RNA structures may be generated for manufacturing purposes or for genetic manipulation, for example. In one embodiment, the RNA structures are utilized to produce a product, for example as a substrate for producing one or more end products from one or more starting products. In one example, a product is manufactured using the RNA structures as a support or scaffold for the process. The RNA structure itself may or may not be modified to incorporate a component of the manufacturing process. In one embodiment the RNA structures are utilized as a structure that contains aptamers to anchor one or more manufacturing components, such as an enzyme or cofactor, for example. In specific embodiments, one or more products are produced in cells that house the RNA structures, including cells that have themselves produced the RNA structures. In one embodiment, RNA structures can be engineered and expressed in cells as cytoskeleton to control the shape of the cells.

In particular embodiments, one or more agents, such as one or more enzymes, are affixed to the structure via an aptamer or a set of aptamers that replaces a kissing loop at the end of an arm in a X, Y, or Z direction, for example. The aptamers can also be embedded in the middle of the arm so that the end of arm is available for other functionalization. RNA structures of any kind may be modified to incorporate one or more enzymes to produce a product. As demonstrated in FIG. 19, highly structured RNA scaffolds may be used to anchor a specific set of enzymes at fixed proximity to maximize efficiency of a biological product. In the specific example therein, oil droplet production may be maximized in green microalga *Chlamydomonas*.

In some cases, one can utilize RNA structures produced by methods of the disclosure to manipulate other nucleic acids, such as regions of cellular DNA, including genomic or mitochondrial DNA. In specific embodiments, highly structured RNA nanostructures may be used to anchor and coat one or more specific regions of one or more chromosomes, thereby shutting down or regulating gene expression at those region(s) s (analogous to X-chromosome inactivation by Xist RNA). This could be achieved by using CRISPR/Cas9 to target guide RNA with embedded subunit to specific genome locations as anchoring 'seeds'. Subsequent polymerization on the anchored seed RNA would lead to the coating of those regions with RNA.

In some cases, one can engineer and express designer RNA structures to build dynamic cytoskeleton system in cells to control the shape of the cells (analogous to actin filaments and microtubules). In specific embodiments, designer RNA cytoskeletons may be used to extend the axons of motor neurons to cross the scar lesion in spinal cord due to spinal cord injury, thus facilitating the re-innervation of muscle cells by motor neurons.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Building Designer RNA Nanostructures for Synthetic Biology Applications

Unlike proteins, RNAs are highly programmable polymers due to their ability to form specific WatsonCrick base pairing, a property that can be exploited to create well-defined 2D and 3D structures. These structures are thermo-dynamically stable, and formed via spontaneous self-assembly, a process that requires no catalytic cofactors.

In contrast to DNA, single-stranded RNA can be efficiently expressed at high levels in live cells, thus offers the opportunity to program cells to assemble designer nanostructures. By careful considering the RNA sequences and RNA domains used, an RNA single unit design was developed that self-assembled into higher order architectures, reaching a size of micrometers. Depending on specific configurations used, these repeating RNA single units assembled spontaneously into precisely organized 1D strings and circles, 1.5D ladders, and 2D grids in isothermal condition without the denature-renature cycles. They are very stable, as they maintained the structural integrity in wet and dry condition. When these RNA single units were expressed in human cells, they appeared to form stable higher order structures. The results represent a first in the field, and lays the technological foundation for genetically encodable higher order RNA nanostructures useful for programing cells to assemble designer nanostructures for specific cellular functions or for synthetic biology applications.

FIGS. 20-27 shows specific examples of RNA subunit structures. They display the modular nature of the subunit with replaceable and extendable arms, loops, and three-way junctions.

Sequences of these examples of structures sequences are provided herein:

19f (SEQ ID NO: 1)
Ggctgcagcttgatcccggcttgagcgctgcgagagcaagccgaagcgg gcacggcttgctctcgctaacgtgtcttcgacggacagcacgagagctg aagccggcacggctctcgtgctgcacaccgaacgcgaagcccgcacgcg ttcggtgtgctaacgttgaagacacggacagcgctcgagccggtcgatc gctgtagcc 22b (SEQ ID NO: 2)
Ggctgcagcagatctagaccgctgccgacgatggcgaagccggcacgcc atcgttggctaacgtgccatgagacggacagctcgctcctagaccgtga acaacaaacgcggtctaggagtgagctgcacaccgaaccgaggtgcaca cggttcggtgtgctaacgtctcgtggcacggacagcggtctggatctgt tgcagcc 24a (SEQ ID NO: 3)
Ggctgcagtgattagtctggtggctcggacagcggtctggacgaagccg gcacgtccagatcgctgccgacgatgagcgaagcgggcacgctcatcgt tggctaacgagtcacctaacgagtgacggacagctcgctcagcgaggtg cacacgctgagtgagctgcacatcgaacgcgaagcccgcacgcgttcgg tgtgctaacgtcgctcggacagactgatcattgcagcc 28a (SEQ ID NO: 4)
Ggctgcagtgattagctggtcagtgcacggacagcggtctggacgaagc gcgcacgtccagatcgctgccgacgatgagcgaagggccacgctcatc gttggctaacgtgcattgacctaacgagacggacagctcgctcagcgaa gccggcacgctgagtgagctgcacatcgaacgcgaggtgcacacgcgtt -continued cggtgtgctaacgtctcggacagctgatcattgcagcc 30a (SEQ ID NO: 5)
Ggctgcagtgattagtctggtagagtctcggacagcggtctggacgaag ccggcacgtccagatcgctgccgacgatgagcgaagcgggcacgctcat cgttggctaacgagattctacctaacgagttgtgacggacagctcgctc agcgaggtgcacacgctgagtgagctgcacatcgaacgcgaagcccgca cgcgttcggtgtgctaacgtcgcaactcggacagactgatcattgcagcc 39a (SEQ ID NO: 6)
Ggctgcagtgattagtctggtagagtctcggacagcggtctggacgagg tgcacacgtccagatcgctgccgacgatgagcgaagcgcgcacgctcat cgttggctaacgagattctacctaacgagttgtgacggacagctcgctc agcgaggtgcacacgctgagtgagctgcacatcgaacgcgaagcgcgca cgcgttcggtgtgctaacgtcgcaactcggacagactgatcattgcagc c 40a (SEQ ID NO: 7)
Ggctgcagtgattagtctggtagagtctcggacagcggtctggacgaag ccggcacgtccagatcgctgccgacgatgagcgaagcgcgcacgctcat cgttggctaacgagattctacctaacgagttgtgacggacagctcgctc agcgaagccggcacgctgagtgagctgcacatcgaacgcgaagcgcgca cgcgttcggtgtgctaacgtcgcaactcggacagactgatcattgcagc c 41a (SEQ ID NO: 8)
Ggctgcagtgattagtctggtagagtctcggacagcggtctggacgaag ccggcacgtccagatcgctgccgacgatgagcgaggtgcacacgctcat cgttggctaacgagattctacctaacgagttgtgacggacagctcgctc agcgaagccggcacgctgagtgagctgcacatcgaacgcgaggtgcaca cgcgttcggtgtgctaacgtcgcaactcggacagactgatcattgcagc c Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

---

What is claimed is:

1. A method of producing a structure in a cell, comprising:
introducing an expression unit into a cell,
- wherein the expression unit comprises a nucleic acid sequence encoding RNA units and a nucleic acid sequence encoding a CRISPR system;
- wherein the RNA units comprise:
  - at least one three-way junction;
  - at least one kissing loop; and
  - a single stranded region;
- wherein the RNA units self-assemble to form the structure,
  - wherein the structure comprises at least two RNA units configured in a pattern of one, two, or three dimensions,
  - wherein the at least two RNA units are bound to each other through complementary binding of a kissing loop on each RNA unit,
  - wherein when the loops are kissing between separate RNA units, the arms of the respective kissing loops from the separate RNA units are at a substantially 180 degree angle.

2. The method of claim 1, wherein the structure binds to a region of a chromosome of the cell or a nucleic acid in an organelle of the cell through the single stranded region of the RNA unit.

3. The method of claim 1,
- wherein the CRISPR system targets the RNA units to the chromosome or nucleic acid in an organelle.

4. A method of producing a structure in a cell, comprising:
introducing, in vitro, a plurality of RNA units into a cell,
- wherein the RNA units comprise:
  - at least one three-way junction;
  - at least one kissing loop; and
  - a single stranded region;
- wherein the RNA units self-assemble to form the structure,
  - wherein the structure comprises at least two RNA units configured in a pattern of one, two, or three dimensions,
  - wherein the at least two RNA units are bound to each other through complementary binding of a kissing loop on each RNA unit,
  - wherein when the loops are kissing between separate RNA units in the plurality, the arms of the respective kissing loops from the separate RNA units are at a substantially 180 degree angle.

5. The method of claim 4, wherein the cell comprises a nucleic acid sequence encoding a CRISPR system.

6. The method of claim 5, wherein upon expression of the nucleic acid encoding the CRISPR system, the CRISPR system targets the RNA units to the chromosome or nucleic acid in an organelle.

7. The method of claim 6, wherein the structure binds to a region of the cell or a nucleic acid in an organelle of the cell through the single stranded region of the RNA unit.

\* \* \* \* \*

SEQUENCE LISTING

```
Sequence total quantity: 18
SEQ ID NO: 1            moltype = RNA   length = 205
FEATURE                 Location/Qualifiers
source                  1..205
                        mol_type = other RNA
                        organism = synthetic construct
SEQUENCE: 1
ggctgcagct tgatcccggc ttgagcgctg cgagagcaag ccgaagcggg cacggcttgc   60
tctcgctaac gtgtcttcga cggacagcac gagagctgaa gccggcacgg ctctcgtgct  120
gcacaccgaa cgcgaagccc gcacgcgttc ggtgtgctaa cgttgaagac acggacagcg  180
ctcgagccgg tcgatcgctg tagcc                                        205

SEQ ID NO: 2            moltype = RNA   length = 203
FEATURE                 Location/Qualifiers
source                  1..203
                        mol_type = other RNA
                        organism = synthetic construct
SEQUENCE: 2
ggctgcagca gatctagacc gctgccgacg atggcgaagc cggcacgcca tcgttggcta   60
acgtgccatg agacggacag ctcgctccta gaccgtgaac aacaaacgcg gtctaggagt  120
gagctgcaca ccgaaccgag gtgcacacgg ttcggtgtgc taacgtctcg tggcacggac  180
agcggtctgg atctgttgca gcc                                          203

SEQ ID NO: 3            moltype = RNA   length = 234
FEATURE                 Location/Qualifiers
source                  1..234
                        mol_type = other RNA
                        organism = synthetic construct
SEQUENCE: 3
ggctgcagtg attagtctgg tggctcggac agcggtctgg acgaagccgg cacgtccaga   60
tcgctgccga cgatgagcga agcgggcacg ctcatcgttg gctaacgagt cacctaacga  120
gtgacggaca gctcgctcag cgaggtgcac acgctgagtg agctgcacat cgaacgcgaa  180
gcccgcacgc gttcggtgtg ctaacgtcgc tcggacagac tgatcattgc agcc        234

SEQ ID NO: 4            moltype = RNA   length = 234
```

```
FEATURE             Location/Qualifiers
source              1..234
                    mol_type = other RNA
                    organism = synthetic construct
SEQUENCE: 4
ggctgcagtg attagctggt cagtgcacgg acagcggtct ggacgaagcg cgcacgtcca   60
gatcgctgcc gacgatgagc gaagggccca cgctcatcgt tggctaacgt gcattgacct  120
aacgagacgg acagctcgct cagcgaagcc ggcacgctga gtgagctgca catcgaacgc  180
gaggtgcaca cgcgttcggt gtgctaacgt ctcggacagc tgatcattgc agcc         234

SEQ ID NO: 5        moltype = RNA   length = 246
FEATURE             Location/Qualifiers
source              1..246
                    mol_type = other RNA
                    organism = synthetic construct
SEQUENCE: 5
ggctgcagtg attagtctgg tagagtctcg gacagcggtc tggacgaagc cggcacgtcc   60
agatcgctgc cgacgatgag cgaagcgggc acgctcatcg ttggctaacg agattctacc  120
taacgagttg tgacggacag ctcgctcagc gaggtgcaca cgctgagtga gctgcacatc  180
gaacgcgaag cccgcacgcg ttcggtgtgc taacgtcgca actcggacag actgatcatt  240
gcagcc                                                              246

SEQ ID NO: 6        moltype = RNA   length = 246
FEATURE             Location/Qualifiers
source              1..246
                    mol_type = other RNA
                    organism = synthetic construct
SEQUENCE: 6
ggctgcagtg attagtctgg tagagtctcg gacagcggtc tggacgaggt gcacacgtcc   60
agatcgctgc cgacgatgag cgaagcgcgc acgctcatcg ttggctaacg agattctacc  120
taacgagttg tgacggacag ctcgctcagc gaggtgcaca cgctgagtga gctgcacatc  180
gaacgcgaag cgcgcacgcg ttcggtgtgc taacgtcgca actcggacag actgatcatt  240
gcagcc                                                              246

SEQ ID NO: 7        moltype = RNA   length = 246
FEATURE             Location/Qualifiers
source              1..246
                    mol_type = other RNA
                    organism = synthetic construct
SEQUENCE: 7
ggctgcagtg attagtctgg tagagtctcg gacagcggtc tggacgaagc cggcacgtcc   60
agatcgctgc cgacgatgag cgaagcgcgc acgctcatcg ttggctaacg agattctacc  120
taacgagttg tgacggacag ctcgctcagc gaagccggca cgctgagtga gctgcacatc  180
gaacgcgaag cgcgcacgcg ttcggtgtgc taacgtcgca actcggacag actgatcatt  240
gcagcc                                                              246

SEQ ID NO: 8        moltype = RNA   length = 246
FEATURE             Location/Qualifiers
source              1..246
                    mol_type = other RNA
                    organism = synthetic construct
SEQUENCE: 8
ggctgcagtg attagtctgg tagagtctcg gacagcggtc tggacgaagc cggcacgtcc   60
agatcgctgc cgacgatgag cgaggtgcac acgctcatcg ttggctaacg agattctacc  120
taacgagttg tgacggacag ctcgctcagc gaagccggca cgctgagtga gctgcacatc  180
gaacgcgagg tgcacacgcg ttcggtgtgc taacgtcgca actcggacag actgatcatt  240
gcagcc                                                              246

SEQ ID NO: 9        moltype = RNA   length = 35
FEATURE             Location/Qualifiers
source              1..35
                    mol_type = other RNA
                    organism = synthetic construct
SEQUENCE: 9
ctcggcttgc tgaagcgcgc acggcaagag gcgag                               35

SEQ ID NO: 10       moltype = RNA   length = 35
FEATURE             Location/Qualifiers
source              1..35
                    mol_type = other RNA
                    organism = synthetic construct
SEQUENCE: 10
ctcggcttgc tgaagcgcgc acggcaagag gcgag                               35

SEQ ID NO: 11       moltype = RNA   length = 16
FEATURE             Location/Qualifiers
source              1..16
                    mol_type = other RNA
                    organism = synthetic construct
```

-continued

```
SEQUENCE: 11
aaaaaaaccc cccccc                                                      16

SEQ ID NO: 12           moltype = RNA    length = 16
FEATURE                 Location/Qualifiers
source                  1..16
                        mol_type = other RNA
                        organism = synthetic construct
SEQUENCE: 12
aaaaaccccc cccccc                                                      16

SEQ ID NO: 13           moltype = RNA    length = 235
FEATURE                 Location/Qualifiers
source                  1..235
                        mol_type = other RNA
                        organism = synthetic construct
SEQUENCE: 13
ggctgcagtg attagtctgg tggctcggac agcggtctgg acgaagccgg cacgtccaga      60
tcgctgccga cgatgagcga agcgggcacg ctcatcgttg ctaacgagt cacctaacga      120
gtgacggaca gctcgctcag cgaggtgcac acgtgagtg agctgcacat cgaacgcgaa      180
gcccgcacgg gttcggtgtg ctaacgtcgc tcggacagac tgatcattgc agccg         235

SEQ ID NO: 14           moltype = RNA    length = 243
FEATURE                 Location/Qualifiers
source                  1..243
                        mol_type = other RNA
                        organism = synthetic construct
SEQUENCE: 14
ggctgcagtg attagtctgg tgagtctcgg acagcggtct ggacgaagcc ggcacgtcca      60
gatcgctgcc gacgatgagc gaagcgggca cgctcatcgt tggctaacga gattcaccta      120
acgagtgtga cggacagctc gctcagcgag gtgcacacgt tgagtgagct gcacatcgaa      180
cgcgaagccc gcacgcgttc ggtgtgctaa cgtcgcactc ggacagactg atcattgcag      240
ccg                                                                   243

SEQ ID NO: 15           moltype = RNA    length = 247
FEATURE                 Location/Qualifiers
source                  1..247
                        mol_type = other RNA
                        organism = synthetic construct
SEQUENCE: 15
ggctgcagtg attagtctgg tagagtctcg gacagcggtc tggacgaagc cggcacgtcc      60
agatcgctgc cgacgatgag cgaagcgggc acgctcatcg ttggctaacg agattctacc      120
taacgagttg tgacggacag ctcgctcagc gaggtgcaca cgctgagtga gctgcacatc      180
gaacgcgaag cccgcacgcg ttcggtgtgc taacgtcgca actcggacag actgatcatt      240
gcagccg                                                               247

SEQ ID NO: 16           moltype = RNA    length = 247
FEATURE                 Location/Qualifiers
source                  1..247
                        mol_type = other RNA
                        organism = synthetic construct
SEQUENCE: 16
ggctgcagtg attagtctgg tagagtctcg gacagcggtc tggacgaggt gcacacgtcc      60
agatcgctgc cgacgatgag cgaagcgcgc acgctcatcg ttggctaacg agattctacc      120
taacgagttg tgacggacag ctcgctcagc gaggtgcaca cgctgagtga gctgcacatc      180
gaacgcgaag cgcgcacgcg ttcggtgtgc taacgtcgca actcggacag actgatcatt      240
gcagccg                                                               247

SEQ ID NO: 17           moltype = RNA    length = 247
FEATURE                 Location/Qualifiers
source                  1..247
                        mol_type = other RNA
                        organism = synthetic construct
SEQUENCE: 17
ggctgcagtg attagtctgg tagagtctcg gacagcggtc tggacgaagc cggcacgtcc      60
agatcgctgc cgacgatgag cgaagcgcgc acgctcatcg ttggctaacg agattctacc      120
taacgagttg tgacggacag ctcgctcagc gaagccggca cgctgagtga gctgcacatc      180
gaacgcgaag cgcgcacgcg ttcggtgtgc taacgtcgca actcggacag actgatcatt      240
gcagccg                                                               247

SEQ ID NO: 18           moltype = RNA    length = 247
FEATURE                 Location/Qualifiers
source                  1..247
                        mol_type = other RNA
                        organism = synthetic construct
SEQUENCE: 18
ggctgcagtg attagtctgg tagagtctcg gacagcggtc tggacgaagc cggcacgtcc      60
agatcgctgc cgacgatgag cgaggtgcac acgctcatcg ttggctaacg agattctacc      120
taacgagttg tgacggacag ctcgctcagc gaagccggca cgctgggtga gctgcacatc      180
```

```
gaacgcgagg tgcacacccg ttcggtgtgc taacgtcgca actcggacag actgatcatt    240
gcagccg                                                              247
```